(12) United States Patent
Neumann

(10) Patent No.: US 11,348,671 B2
(45) Date of Patent: May 31, 2022

(54) METHODS AND SYSTEMS FOR SELECTING A PRESCRIPTIVE ELEMENT BASED ON USER IMPLEMENTATION INPUTS

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 48 days.

(21) Appl. No.: 16/589,066

(22) Filed: Sep. 30, 2019

(65) Prior Publication Data

US 2021/0098101 A1    Apr. 1, 2021

(51) Int. Cl.
*G16H 20/10* (2018.01)
*G16H 50/20* (2018.01)
(Continued)

(52) U.S. Cl.
CPC ............. *G16H 20/10* (2018.01); *G16H 10/60* (2018.01); *G16H 50/20* (2018.01); *G16H 50/30* (2018.01); *H04L 67/12* (2013.01)

(58) Field of Classification Search
CPC ........ G16H 10/60; G16H 50/20; G16H 20/10; G16H 50/30; G06F 15/173; C12Q 1/6883; C12Q 2600/156
(Continued)

(56) References Cited

U.S. PATENT DOCUMENTS 8,655,682 B2   2/2014   Srivastava et al.
8,655,817 B2   2/2014   Hasey et al.
(Continued)

FOREIGN PATENT DOCUMENTS

WO   2018200806   11/2018
WO   2019144116   7/2019

OTHER PUBLICATIONS

Katzman et al.; "Deepsurv: Personalized Treatment Recommender System Using a Cox Proportional Hazards Deep Neural Network"; Aug. 9, 2017; https://arxiv.org/pdf/1606.00931.pdf.

*Primary Examiner* — Mark Holcomb
(74) *Attorney, Agent, or Firm* — Caldwell Intellectual Property Law; Katherine Rubino

(57) ABSTRACT

A system for selecting a prescriptive element based on user implementation inputs. The system includes at least a computing device and a prescriptive generator module operating on the at least a computing device. A prescriptive generator module is configured to receive at least a diagnosis descriptor from a user client device, receive prescriptive training data, and generate using a supervised machine-learning process a prescriptive model that produces an output containing a plurality of prescriptive elements. The system includes a loss function module operating on the at least a computing device. The loss function module is configured to receive from a user client device at least a user implementation response and generate a loss function as a function of the at least a user implementation response and the plurality of prescriptive elements. The loss function module minimizes the loss function and selects a prescriptive element as a function of minimizing the loss function. The loss function module transmits the selected prescriptive element to a user client device.

16 Claims, 10 Drawing Sheets

(51) Int. Cl.
*G16H 50/30* (2018.01)
*G16H 10/60* (2018.01)
*H04L 67/12* (2022.01)

(58) Field of Classification Search
USPC .................................................... 705/2–4
See application file for complete search history.

(56) References Cited

U.S. PATENT DOCUMENTS

| | | | |
|---|---|---|---|
| 10,140,422 B2 | 11/2018 | Rust et al. | |
| 2004/0243433 A1* | 12/2004 | Akin | G06F 17/60 |
| | | | 705/2 |
| 2007/0027636 A1* | 2/2007 | Rabinowitz | G06Q 50/22 |
| | | | 702/20 |
| 2008/0172214 A1* | 7/2008 | Col | G06Q 50/24 |
| | | | 703/11 |
| 2012/0016690 A1* | 1/2012 | Ramarajan | G16H 15/00 |
| | | | 705/2 |
| 2014/0244292 A1* | 8/2014 | Rosenberg | G06F 19/324 |
| | | | 705/2 |
| 2014/0278453 A1 | 9/2014 | Primack et al. | |
| 2015/0088534 A1 | 3/2015 | Spertus | |
| 2015/0254408 A1* | 9/2015 | Dadlani Mahtani | G16H 50/20 |
| | | | 705/2 |
| 2016/0070867 A1* | 3/2016 | Zhang | G06F 17/289 |
| | | | 705/2 |
| 2017/0177822 A1 | 6/2017 | Fogel | |
| 2017/0329917 A1* | 11/2017 | McRaith | G16H 50/20 |
| 2018/0330059 A1 | 11/2018 | Bates et al. | |
| 2019/0043610 A1 | 2/2019 | Vaughan | |
| 2019/0108912 A1 | 4/2019 | Spurlock, III et al. | |
| 2019/0130069 A1 | 5/2019 | Li et al. | |
| 2019/0214145 A1 | 7/2019 | Kurek | |
| 2019/0279767 A1 | 9/2019 | Bates | |

\* cited by examiner

METHODS AND SYSTEMS FOR SELECTING A PRESCRIPTIVE ELEMENT BASED ON USER IMPLEMENTATION INPUTS

FIELD OF THE INVENTION

The present invention generally relates to the field of artificial intelligence. In particular, the present invention is directed to methods and systems for selecting a prescriptive element based on user implementation inputs.

BACKGROUND

Accurate and informed selection of prescriptive elements can be difficult to implement. A multitude of variables need to be analyzed and accounted for. Incorrect selection of prescriptive elements can cause fruitless spending on unnecessary treatments that may contribute to further health deterioration.

SUMMARY OF THE DISCLOSURE

In an aspect, a system for selecting a prescriptive element based on user implementation inputs. The system includes at least a computing device wherein the at least a computing device further comprises one or more network interfaces; a non-volatile memory; and including one or more processors. The system includes a prescriptive generator module operating on the at least a computing device, the prescriptive generator module designed and configured to receive at least a diagnosis descriptor from a user client device wherein the at least a diagnosis descriptor contains a current or future probable medical condition; receive prescriptive training data from a machine-learning database correlating at least a diagnosis descriptor to at least a prescriptive element; and generate using a supervised machine-learning process a prescriptive model that receives the at least a diagnosis descriptor as an input and produces an output containing a plurality of prescriptive elements. The system includes a loss function module operating on the at least a computing device, the loss function module designed and configured to receive from a user client device at least a user implementation response wherein the at least a user implementation response contains at least a prescriptive element indicator; receive the at least a diagnosis descriptor and the plurality of prescriptive elements from the prescriptive generator module; generate a loss function as a function of the at least a user implementation response and the plurality of prescriptive elements; minimize the loss function; select a prescriptive element as a function of minimizing the loss function; and transmit the selected prescriptive element to the user client device.

In an aspect, a method of selecting a prescriptive element based on user implementation inputs. the method includes receiving by at least a computing device at least a diagnosis descriptor from a user client device wherein the at least a diagnosis descriptor contains a current or future probable medical condition. The method includes receiving by the at least a computing device prescriptive training data from a machine-learning database correlating at least a diagnosis descriptor to at least a prescriptive element. The method includes generating by the at least a computing device using a supervised machine-learning process a prescriptive model that receives the at least a diagnosis descriptor as an input and produces an output containing a plurality of prescriptive elements. The method includes receiving by the at least a computing device from a user client device at least a user implementation response wherein the at least a user implementation response contains at least a prescriptive element indicator. The method includes receiving by the at least a computing device the at least a diagnosis descriptor and the plurality of prescriptive elements from the prescriptive generator module. The method includes generating by the at least a computing device a loss function as a function of the at least a user implementation response and the plurality of prescriptive elements. The method includes minimizing by the at least a computing device the loss function. The method includes selecting by the at least a computing device a prescriptive element as a function of minimizing the loss function. The method includes transmitting by the at least a computing device the selected prescriptive element to the user client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for selecting a prescriptive element based on user implementation inputs. In an embodiment, at least a computing device receives at least a diagnosis descriptor from a user client device containing a current for future probable medical condition. At least a computing device receives prescriptive training data from a machine-learning database correlating at least a diagnosis descriptor to at least a prescriptive element. At least a computing device generates using a supervised machine-learning process a prescriptive model that receives at least a diagnosis descriptor as an input and produces an output containing a plurality of prescriptive elements. At least a computing device receives from a user client device at least a user implementation response containing at least a prescriptive element indicator. At least a computing device generates a loss function as a function of at least a user implementation response and the plurality of prescriptive elements. At least a computing device minimizes the loss function and selects a prescriptive element as a function of minimizing the loss function. At least a computing device transmits the selected prescriptive element to a user client device.

Figure 1:
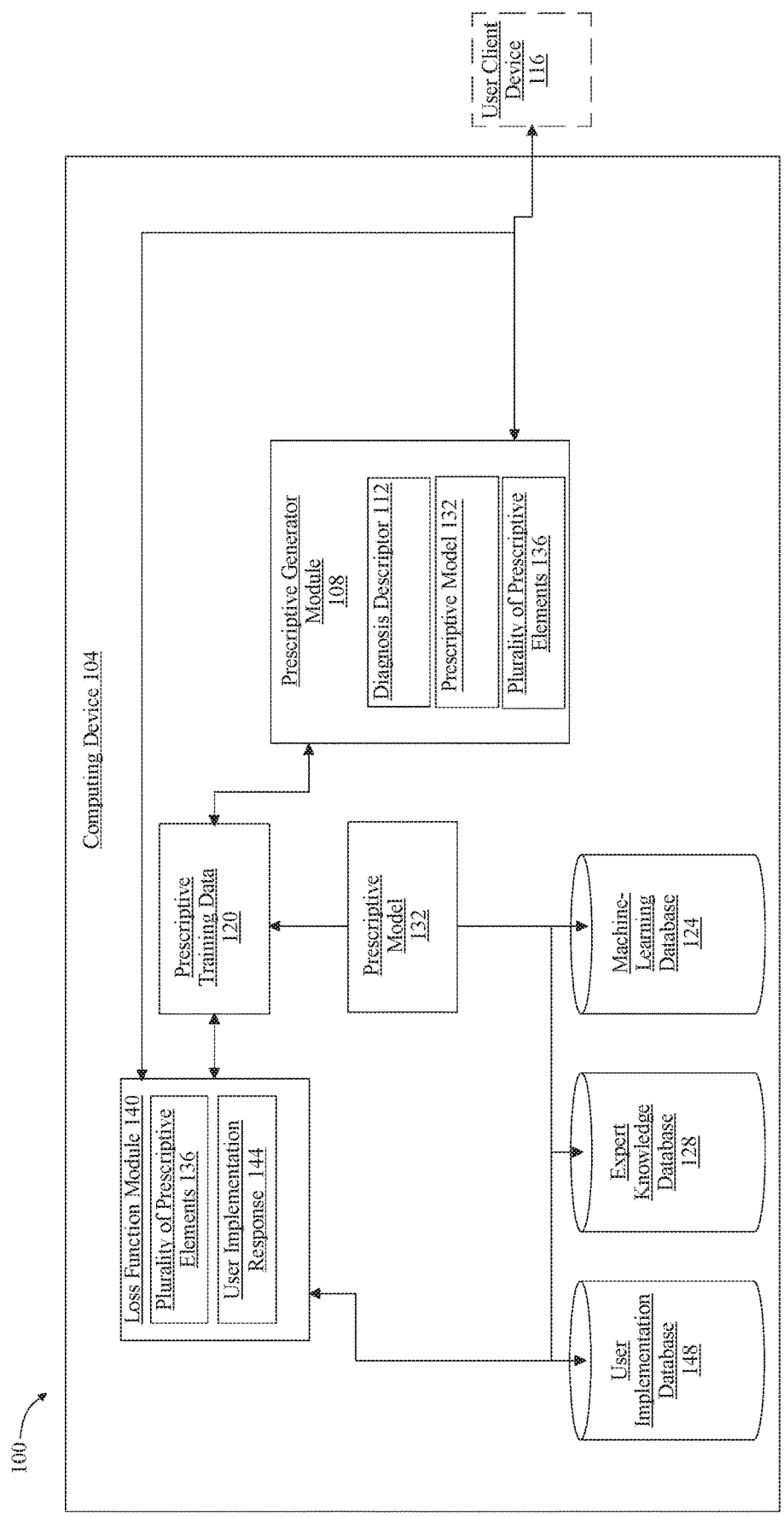
FIG. 1 is a block diagram illustrating an exemplary embodiment of a system for selecting a prescriptive element based on user implementation inputs.

Referring now to FIG. 1, an exemplary embodiment of a system for selecting a prescriptive element based on user implementation inputs is illustrated. System 100 includes at least a computing device 104, wherein the at least a computing device 104 further comprises one or more network interfaces, a non-volatile memory, and including one or more processors. Computing device 104, as used herein, includes any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include at least a server. At least a server may include a single computing device 104 operating independently or may include two or more computing device 104 operating in concert, in parallel, sequentially or the like; two or more computing device 104 may be included together in a single computing device 104 or in two or more computing device 104. At least a server may interact with one or more additional devices as described below in further detail via a network interface device. Network interface device may be utilized for connecting at least a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network may employ a wired and/or a wireless mode of communication. In general, any network topology may be used. Information (e.g., data, software etc.) may be communicated to and/or from a computer and/or a computing device 104. At least a server may include but is not limited to, for example, a computing device 104 or cluster of computing device 104 in a first location and a second computing device 104 or cluster of computing device 104 in a second location. At least a server may include one or more computing device 104 dedicated to data storage, security, distribution of traffic for load balancing, and the like. At least a server may distribute one or more computing tasks as described below across a plurality of computing device 104 of computing device 104, which may operate in parallel, in series, redundantly, or in any other manner used for distribution of tasks or memory between computing device 104. At least a server may be implemented using a "shared nothing" architecture in which data is cached at the worker, in an embodiment, this may enable scalability of system 100 and/or computing device 104.

With continued reference to FIG. 1, at least a computing device 104 may be designed and/or configured to perform any method, method step, or sequence of method steps in any embodiment described in this disclosure, in any order and with any degree of repetition. For instance, at least a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a prescriptive generator module 108 operating on at least a computing device. Prescriptive generator module 108 may include any hardware and/or software module. Prescriptive generator module 108 is configured to receive at least a diagnosis descriptor 112 from a user client device 116 wherein the at least a diagnosis descriptor 112 contains a current or future probable health condition, receive prescriptive training data 120 from a machine-learning database 124 correlating at least a diagnosis descriptor 112 to at least a prescriptive element, and generate using a supervised machine-learning process a prescriptive model 132 that receives the at least a diagnosis descriptor 112 as an input and produces an output containing a plurality of prescriptive elements 136.

With continued reference to FIG. 1, prescriptive generator module 108 is configured to receive at least a diagnosis descriptor 112 from a user client device 116 wherein the at least a diagnosis descriptor 112 contains a current future probable health condition. A "diagnosis descriptor 112" as used in this disclosure, includes an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a diagnosis descriptor 112 may be associated with a physical and/or somatic condition, a mental condition such as a mental illness, neurosis, or the like, or any other condition affecting human health that may be associated with one or more elements of physiological state data. Conditions associated with diagnosis descriptor 112 may include, without limitation one or more diseases, defined for purposes herein as conditions that negatively affect structure and/or function of part or all of an organism. Conditions associated with diagnosis descriptor 112 may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Diagnosis descriptor 112 may be associated with one or more immune disorders, including without limitation immunodeficiencies and/or auto-immune conditions. Diagnosis descriptor 112 may be associated with one or more metabolic disorders. Diagnosis descriptor 112 may be associated with one or more endocrine disorders. Diagnosis descriptor 112 may be associated with one or more cardiovascular disorders. Diagnosis descriptor 112 may be associated with one or more respiratory disorders. Diagnosis descriptor 112 may be associated with one or more disorders affecting connective tissue. Diagnosis descriptor 112 may be associated with one or more digestive disorders. Diagnosis descriptor 112 may be associated with one or more neurological disorders such as neuromuscular disorders, dementia, or the like. Diagnosis descriptor 112 may be associated with one or more disorders of the excretory system, including without limitation nephrological disorders. Diagnosis descriptor 112 may be associated with one or more liver disorders. Diagnosis descriptor 112 may be associated with one or more disorders of the bones such as osteoporosis. Diagnosis descriptor 112 may be associated with one or more disorders affecting joints, such as osteoarthritis, gout, and/or rheumatoid arthritis. Diagnosis descriptor 112 be associated with one or more cancers, including without limitation carcinomas, lymphomas, leukemias, germ cell tumor cancers, blastomas, and/or sarcomas. Diagnosis descriptor 112 may include descriptors of latent, dormant, and/or apparent disorders, diseases, and/or conditions. Diagnosis descriptor 112 may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with diagnosis descriptor 112 as described in this disclosure.

Still referring to FIG. 1, at least a diagnosis descriptor 112 may be stored in any suitable data and/or data type. For instance, and without limitation, at least a diagnosis descriptor 112 may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a diagnosis descriptor 112 may take; persons skilled in the art, upon reviewing the entirety of this disclosure, will be aware of various forms which may be suitable for use as at least a diagnosis descriptor 112 consistently with this disclosure.

With continued reference to FIG. 1, at least a diagnosis descriptor 112 is received from a user client device 116. User client device 116 may include, without limitation, a display in communication with at least a server, display may include any display as described here. User client device 116 may include an additional computing device, such as a mobile device, laptop, desktop computer, or the like; as a non-limiting example, user client device 116 may be a computer and/or workstation operated by a medical professional. Output may be displayed on at least a user client device 116 using an output graphical user interface.

With continued reference to FIG. 1, prescriptive generator module 108 is configured to receive prescriptive training data 120 from a machine-learning database 124 correlating at least a diagnosis descriptor 112 to at least a prescriptive element. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server 104 may correlate any input data as described in this disclosure to any output data as described in this disclosure.

With continued reference to FIG. 1, prescriptive generator module 108 receives training data correlating at least an element of diagnosis descriptor 112 data to at least a prescriptive element. "Correlation" in a training data set may include any relation established therein linking one datum to another, including inclusion together in a data element, row, column, cell, or the like, and/or by giving each a common indicator and/or label indicative of their correlation in data used to create and/or compile training data. Correlation may include a relation established whereby at least an element of diagnosis descriptor 112 data is correlated to at least a prescriptive element based on data entries obtained from the same subject. Training set may include a plurality of entries, each entry correlating at least an element of diagnostic data to at least a prescriptive element.

With continued reference to FIG. 1, prescriptive training data 120 is received from a machine-learning database 124. Machine-learning database 124 may include any data structure for ordered storage and retrieval of data, which may be implemented as a hardware or software module. Machine-learning database 124 may be implemented, without limitation, as a relational database, a key-value retrieval datastore such as a NOSQL database, or any other format or structure for use as a datastore that a person skilled in the art would recognize as suitable upon review of the entirety of this disclosure. Machine-learning database 124 may include input from experts regarding prescriptive training sets and/or prescriptive model 132 as described in more detail below.

With continued reference to FIG. 1, system 100 may include expert knowledge database 128. Expert knowledge database 128 may include any data structure suitable for use as machine-learning database 124 as described above. Expert knowledge database 128 may include entries from experts as described in more detail below.

With continued reference to FIG. 1, prescriptive generator module 108 is configured to receive at least a diagnosis descriptor 112 containing a disease classifier wherein the disease classifier includes a disease stage descriptor and receive prescriptive training data 120 from a machine-learning database 124 as a function of the at least a disease stage descriptor. A "disease classifier" as used in this disclosure, includes an indicator labeling topographic body region and/or body system impacted by a particular disease. Topographic body region may include a particular anatomical body region impacted by a disease. For instance and without limitation, a disease such as migraine may contain a disease classifier such as "head and neck." In an embodiment, a disease may impact one or more body regions. In the previous example, a disease such as migraine may contain a second disease classifier such as "frontal" when migraines are located on the forehead. Disease classifier may indicate a particular body system impacted by a particular disease. Body system may include a particular organ system including for example, circulator system, digestive system, endocrine system, integumentary system, immune system, lymphatic system, muscular system, nervous system, renal system, urinary system, reproductive system, respiratory system, skeletal system, and/or hematopoietic system. For example, a disease such as migraine may impact the nervous system while a disease such as ulcerative colitis may impact the digestive system. Disease classifier includes a disease stage descriptor. A "disease stage descriptor" as used in this disclosure, includes an indicator describing the extent to which a particular disease has developed by progressing, spreading, and potentially creating other disease states. In an embodiment, disease stage descriptor may include a numerical score indicating how far a particular disease has developed, whereby a higher numerical score may indicate a particular disease has further developed. In an embodiment, each disease may contain its own numerical scoring system. For instance and without limitation, a disease such as rheumatoid arthritis may contain a disease stage descriptor of stage 3 when rheumatoid arthritis has advanced to affect two or more joints. In yet another non-limiting example, a disease such as Chron's disease may contain a disease stage descriptor of stage 3 when Chron's disease has advanced to cause four or more flares each year.

With continued reference to FIG. 1, prescriptive generator module 108 receives training data from machine-learning database 124 as a function of at least a disease stage descriptor. Machine-learning database 124 may include training sets and/or machine-learning models including prescriptive model 132 organized by disease state, disease classifier, and/or disease stage descriptor that may be utilized to select a training set and/or machine-learning model as described in more detail below.

With continued reference to FIG. 1, prescriptive generator module 108 receives prescriptive training data 120 that includes at least a prescriptive element. A "prescriptive element" as used in this disclosure, includes any data that identifies a process that improves a current, incipient, or probable future medical condition affecting a person identified using a diagnosis descriptor 112. Prescriptive processes may include, without limitation, exercise programs, including amount, intensity, and/or types of exercise recommended. Prescriptive processes may include, without limitation, dietary or nutritional recommendations based on data including nutritional content, digestibility, or the like. Prescriptive processes may include one or more medical procedures. Prescriptive processes may include one or more physical, psychological, or other therapies. Prescriptive processes may include one or more medications, supplements, homeopathic remedies, herbs, therapies, and the like. For instance and without limitation, a prescriptive element may include a medication a user may take by mouth to lower cholesterol or an exercise regimen user may practice three times each week that includes swimming two miles three times each week to ease joint pain from arthritis. Persons skilled in the art, upon reviewing the entirety of this disclosure, will be aware of various processes that may be used as prescriptive processes consistently with this disclosure.

With continued reference to FIG. 1, prescriptive generator module 108 is configured to generate using a supervised machine-learning process a prescriptive model 132 that receives at least a diagnosis descriptor 112 as an input and produces an output containing a plurality of prescriptive elements 136. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of diagnosis descriptor 112 as inputs, prescriptive elements as outputs, and a scoring function representing a desired form of relationship to be detected between elements of diagnosis descriptor 112 and prescriptive elements; scoring function may, for instance, seek to maximize the probability that a given element of diagnostic data and/or combination of elements of diagnostic data is associated with a given prescriptive element and/or combination of prescriptive elements to minimize the probability that a given element of diagnostic data and/or combination of elements of diagnostic data is not associated with a given prescriptive element and/or combination of prescriptive elements. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between elements of diagnosis descriptor 112 and prescriptive elements. In an embodiment, one or more supervised machine-learning algorithms may be restricted to a particular domain for instance, a supervised machine-learning process may be performed with respect to a given set of parameters and/or categories of parameters that have been suspected to be related to a given set of diagnostic data, and/or are specified as linked to a medical specialty and/or field of medicine covering a particular set of diagnostic data. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various prescriptive elements; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate diagnostic data. Additional supervised learning processes may be performed without domain restrictions to detect, for instance, previously unknown and/or unsuspected relationships between diagnostic data and prescriptive elements.

With continued reference to FIG. 1, prescriptive generator module 108 is configured to generate using a supervised machine-learning processes a prescriptive model 132 that outputs a plurality of prescriptive elements 136. Supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

Still referring to FIG. 1, machine-learning processes as described in this disclosure may be used to generate machine-learning models. A "machine-learning model," as used in this disclosure, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, for instance for multi-layered networks.

With continued reference to FIG. 1, prescriptive generator module is configured to transmit the plurality of prescriptive elements to a user client device wherein the plurality of prescriptive elements each contain a prescriptive allocation resource calculation. A "prescriptive allocation resource calculation" as used in this disclosure, includes any information regarding total user cost and/or price for a particular prescriptive element. Prescriptive generator module is configured to transmit the plurality of prescriptive elements generated by prescriptive generator module to a user client device to allow a user to see what the cost and/or price may be for a particular treatment. This may help a user to make informed decisions and evaluate the thoroughness of the user's medical professional who may be treating the patient. This can also help a user better plan and understand the user's short term versus long term financial goas. For example, if a user receives information that about the high price of a particular treatment over the long term, then the user may be able to save more money in the short term to compensate for what he or she will spend in the long term. Ultimately this may also help a user create more trust in the healthcare system and ensure that are not receiving unnecessary costly treatments.

With continued reference to FIG. 1, system 100 includes a loss function module 140 operating on at least a computing device. Loss function module 140 may include any hardware and/or software module. Loss function module 140 is designed and configured to receive from a user client device 116 at least a user implementation response 144 wherein the at least a user implementation response 144 contains at least a prescriptive element indicator, receive from the prescriptive generator module 108 at least a diagnosis descriptor 112 and a plurality of prescriptive elements 136, generate a loss function as a function of the at least a user implementation response 144 and the plurality of prescriptive elements 136, minimize the loss function, select a prescriptive element as a function of minimizing the loss function and transmit the selected prescriptive element to the user client device 116.

With continued reference to FIG. 1, loss function module 140 may perform machine-learning algorithms using a loss function analysis utilizing linear regression to select a prescriptive element from a plurality of prescriptive elements 136 utilizing user implementation response 144. A "user implementation response" as used in this disclosure, includes data describing a user's response towards one or more parameters necessary to implement prescriptive elements. Parameters necessary to implement prescriptive elements include factors such as cost of treatment, ability to travel to a treatment center, user mobility, difficulty to implement, immediate treatment results versus long term analysis, root cause disease reversal, insurance coverage of a treatment, and the like. At least a user implementation response 144 contains at least a prescriptive element indicator. A "prescriptive element indicator" as used in this disclosure, includes data describing an ideal prescriptive element for a user. Ideal prescriptive element may include a descriptive of an optimal treatment that a user is willing to utilize and/or perform for a particular diagnosis descriptor 112. Optimal treatment may include a treatment that a user feels is most convenient and/or a treatment that a user is willing to adhere to and perform. For instance and without limitation, a prescriptive element indicator may include data describing a user's ideal prescriptive element as being able to swallow a pill once per day to treat user's Type 2 Diabetes Mellitus. In yet another non-limiting example, a prescriptive element indicator may include data describing a user's ideal prescriptive element as having user engage in physical activity three days each week for 30 minutes to treat user's high risk for cardiovascular disease. User implementation response 144 may be stored and maintained in user implementation database 148 as described in more detail below.

With continued reference to FIG. 1, user implementation response 144 may include a response containing a prescriptive allocation standard response. A "prescriptive allocation standard response" as used in this disclosure includes a user response containing a description of the total amount of resources that a user is willing to devote to a prescriptive element. Resources may include a budget, and/or total out of pocket dollar amount that a user may devote to a prescriptive element for a particular length of time. For example, a user may enter a total budget amount that a user is willing to spend on developing a yoga practice including paying for yoga classes, clothes suitable to be worn to yoga, yoga equipment that may be needed as well as transportation costs to yoga classes. In yet another non-limiting example, a user may enter a total dollar amount that user may wish to spend on a prescriptive element such as a user who is willing to spend $50 per month on supplements. Prescriptive allocation standard response may include a prescriptive allocation estimation containing a treatment stage factor multiplied by a treatment length factor and a treatment accessibility factor. A "prescriptive allocation estimation" as used in this disclosure, includes a description of an approximation of what a user is willing to pay for a particular course of treatment for a particular disease state. Prescriptive allocation estimation includes a treatment stage factor which includes an indication of what treatment stage a user may be experiencing. Treatment stage factor may include categories that include treatment naive for a user who has never been treated for a particular disease state before, treatment failure for a user who has previously failed other treatments for a particular disease, and treatment response for a user who has responded to treatment. Treatment stage may indicate what stage of treatment a particular user has experienced. Prescriptive allocation estimation includes a treatment length factor which indicates how long treatment may be warranted for. Treatment length may include a description that indicates how much time treatment may be needed for. Treatment length may include potential responses that include short-term when treatment may be needed for less than two weeks; intermediate term when treatment may be needed for more than two weeks but less than six months; foreseeable future when treatment may be needed for more than six months but less than one year, and indefinite when treatment may be necessary for more than one year. Prescriptive allocation estimation includes a treatment accessibility factor which includes an indication of how accessible treatment is for a user. Accessible treatment may include the ease with which a user is able to obtain treatment. Accessible treatment may include how treatment dense a particular geographic region may be and how many medical professionals may be located in a given area. For example, a user who lives in a metropolitan area such as New York City may have treatments readily accessible while a user who lives on a farm in Kansas may not have treatments available.

With continued reference to FIG. 1, user implementation response 144 may include a numerical response reflecting a user willingness indicator containing an effort factor. A "user willingness indicator" as used in this disclosure, includes an element of data describing a user's willingness to partake in a particular prescriptive element. User willingness indicator includes a numerical response, with a higher numerical response indicating a user having more willingness to partake in a particular prescriptive element. For instance and without limitation, a user willingness indicator may include a user's willingness to develop and implement a yoga practice three days each week. In yet another non-limiting example a user willingness indicator may include a user's willingness to take an herbal supplement three times per day for a minimum of one year course of treatment. User willingness indicator may include an effort descriptor. An "effort descriptor" as used in this disclosure, includes a description of the amount of effort that a user may be willing to devote to a particular prescriptive element. Effort descriptor may include a textual description such as if a user is willing to devote a small amount of effort towards exercise or may contain a numerical score with a higher score indicating a higher level of effort that is likely to be given. In an embodiment, a numerical score may be based on a set numerical score with a range between 0-100, where a score of zero indicates no effort that is likely to be given whereby a score of 100 indicates the most effort that can be given.

With continued reference to FIG. 1, loss function module 140 may compare one or more user implementation response 144 to a mathematical expression representing an optimal combinations of user implementation response 144 and/or optimal prescriptive elements. Mathematical expression may include a linear combination of variables, weighted by coefficients representing relative importance of each variable in selecting an optimal prescriptive element. For instance, a variable such as cost may be multiplied by a first coefficient representing the importance of cost, a second user input such as user mobility may be multiplied by a second coefficient representing the importance of user mobility, a degree of variance from a prescriptive element may be represented as another parameter, which may be multiplied by another coefficient representing the importance of that variable; persons skilled in the art, upon reviewing the entirety of this disclosure, will be aware of different variables that may be weighted by various coefficients. Use of a linear combination is provided only as an illustrative example; other mathematical expressions may alternative or additionally be used, including without limitation higher-order polynomial expressions or the like.

With continued reference to FIG. 1, mathematical expression may represent a loss function where a "loss function" is an expression of an output of which an optimization algorithm minimizes to generate an optimal result. As a non-limiting example, loss function module 140 may calculate variables of each of a plurality of user implementation response 144 and/or prescriptive elements, calculate an output of mathematical expression using the variables, and select at least a prescriptive element that produces an output having the lowest size, according to a given definition of "size," of the sets of outputs representing each of the plurality of prescriptive elements 136; size may, for instance, include absolute value, numerical size, or the like. Selection of different loss functions may result in identification of different prescriptive elements as generating minimal outputs; for instance, where a user implementation response 144 such as cost is associated in a first loss function with a large coefficient or weight, a user input such as user mobility having a small coefficient or weight may minimize the first loss function, whereas a second loss function where cost has a smaller coefficient but degree of variance from user mobility may produce a minimal output for a different prescriptive element having a larger coefficient for cost response but more closely hewing to user mobility.

With continued reference to FIG. 1, each prescriptive element of the plurality of prescriptive elements 136 may be represented by a mathematical expression having the same form as mathematical expression; loss function module 140 may compare the former to the latter using an error function representing average difference between the two mathematical expressions. Error function may, as a non-limiting example, be calculated using the average difference between coefficients corresponding to each user input variables. A prescriptive element having a mathematical expression minimizing the error function may be selected, as representing an optimal expression of relative importance of variables to a system or user. In an embodiment, error function and loss function calculations may be combined; for instance, a prescriptive element resulting in a minimal aggregate expression of error function and loss function, such as a simple addition, arithmetic mean, or the like of the error function with the loss function, may be selected, corresponding to an option that minimizes total variance from optimal variables while simultaneously minimizing a degree of variance from a set of priorities corresponding to ameliorative output variables. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each variable to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function: i.e., regression. Mathematical expression and/or loss function be user-specific, using a training set composed of past user selections; may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of user implementation response 144.

With continued reference to FIG. 1, generating loss function includes evaluating at least a user implementation factor wherein the user implementation factor contains a numerical scored response, assigning a weighted variable to the at least a user implementation response 144 as a function of the user implementation factor and minimize the loss function as a function of the weighted variable. A "user implementation factor" as used in this disclosure, includes a numerical score reflecting the importance of a user implementation response 144 as compared to other user implementation response 144. A numerical score that contains a higher number may indicate a higher level of importance of a given user implementation factor. A numerical scored response may be generated by a user and may reflect the importance of a user implementation response to a particular user. For instance and without limitation, a user may score a user implementation factor such as inability to travel far to a treatment center as being more important than the cost of treatment because the user doesn't have access to reliable transportation and is unable to drive oneself. In yet another non-limiting example, a user may score a user implementation factor such as user mobility indicating user is highly mobile and can get to treatment without assistance from others are more important over cost because user is on a restricted budget. Loss function module 140 assign a weighted variable to at least a user implementation response 144 as a function of the user implementation factor. A "weighted variable" as used in this disclosure, includes a value or weight for each observation in a user implementation response. In an embodiment, a user implementation response that has a larger weighted variable may have more influence as compared to a user implementation response that has a smaller weighted variable response. For instance and without limitation, loss function module 140 may assign a larger weighted variable to a user implementation response 144 that contains a higher numerical scored response to a user implementation optimization factor while loss function module 140 may assign a smaller weighted variable to a user implementation response 144 that contains a lower numerical scored response to a user implementation optimization factor. Loss function module 140 minimizes the loss function as a function of the weighted variable. Loss function module 140 may classify at least a user implementation response 144 as a function of the numerical scored response. Classification may include sorting user implementation response 144 into particular categories containing shared characteristics as a function of user implementation factor containing a numerical scored response. Numerical scored response may be matched to a particular category that may Categories may include "optimal" for those user implementation factors containing the highest numerical scored response. Categories may include "average" for those user implementation factors containing an average numerical scored response. Categories may include "low" for those user implementation factors containing a low numerical scored response. In an embodiment, loss function module 140 may be programed to know what numerical score ranges may fit within each defined category. Loss function module 140 may generate a classification label indicating a user implementation optimization factor as a function of the numerical scored response. Classification label may include data describing which category a particular user implementation response 144 belongs to. Classification label may be generated utilizing a supervised machine-learning model that may be trained to match an input a particular category and classify it. Classification may be performed utilizing classification algorithms that include for example logistic regression, naïve bayes classifier, k-nearest neighbor, support vector machines, decision trees, boosted trees, random forest, and/or neural networks. Loss function module 140 selects at least a user implementation response 144 containing an "optimal" classification label and minimizes the total variance from the at least a user implementation response 144 containing an optimal classification label.

With continued reference to FIG. 1, loss function module 140 may minimize a loss function by generating a plurality of user implementation neutralizer. A "user implementation neutralizer" as used in this disclosure, includes a user implementation response 144 that contains a smaller weighted variable score intended to help minimize a user implementation response 144 containing a larger weighted variable score. Loss function module 140 may generate a plurality of user implementation neutralizers by selecting user implementation response 144 that contain a low weighted variable score and/or are classified as containing a "low" and/or "average" classification labels. Loss function module 140 may transmit the plurality of user implementation neutralizers to a user client device 116 and receive a user implementation neutralizer response from the user client device 116. User implementation neutralizer response may include a user response describing which of the plurality of user implementation neutralizers user deems to be of least importance. For instance, user response may indicate that a user deems from a plurality of user implementation neutralizers that a user implementation neutralizer such as travel time is of least importance to user. Loss function module 140 selects a user implementation neutralizer as a function of the user implementation neutralizer response and minimizes the loss function utilizing the selected user implementation neutralizer.

Figure 2:
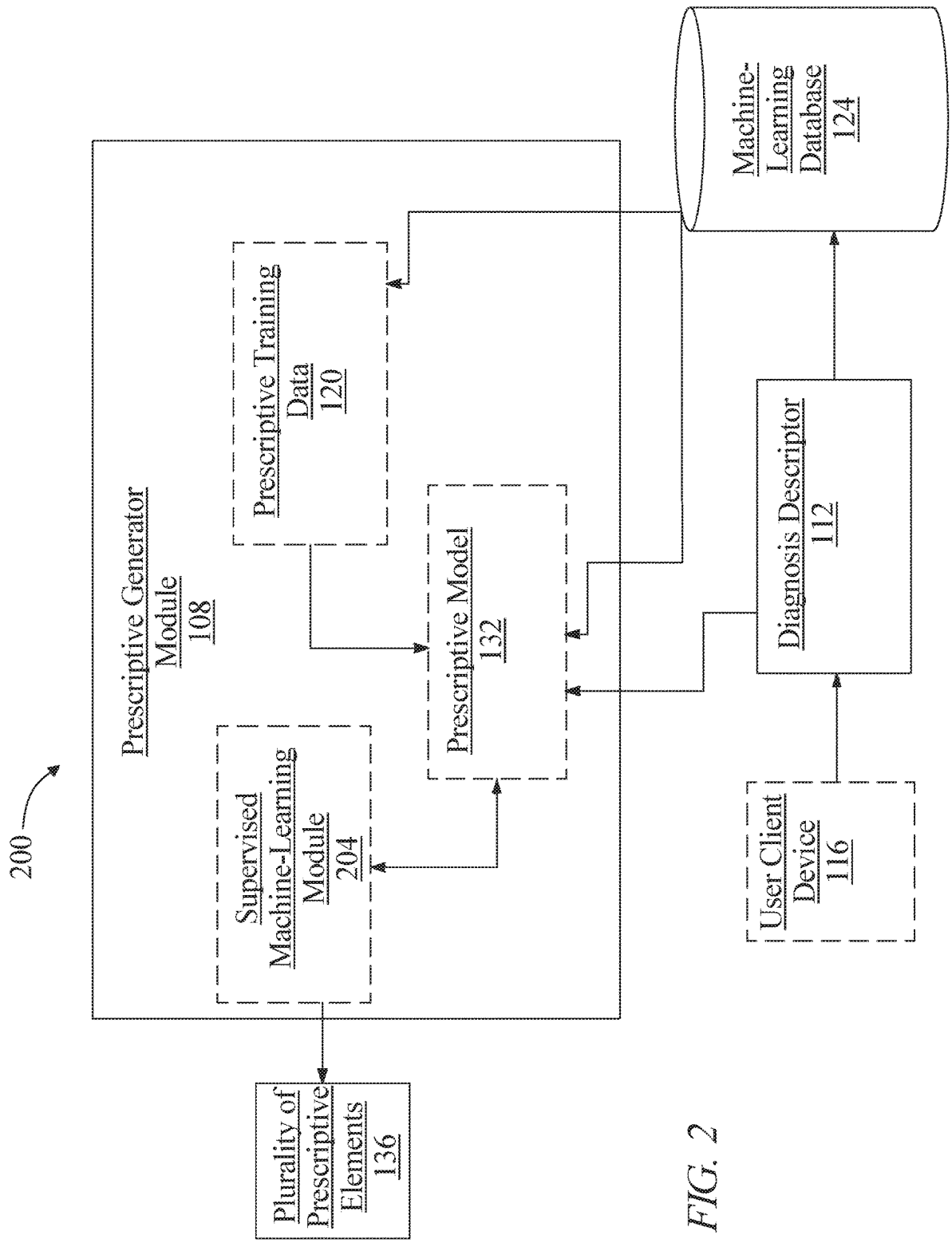
FIG. 2 is a block diagram illustrating an exemplary embodiment of a prescriptive generator module.

Referring now to FIG. 2, an exemplary embodiment 200 of a prescriptive generator module 108 is illustrated. Prescriptive generator module 108 may be implemented as a hardware or software module. Prescriptive generator module 108 is configured to receive at least a diagnosis descriptor 112 from a user client device 116 wherein the at least a diagnosis descriptor 112 contains a current or future probable medical condition, receive prescriptive training data 120 from a machine-learning database 124 correlating at least a diagnosis descriptor 112 to at least a prescriptive element; generate using a supervised machine-learning process a prescriptive model 132 that receives the at least a diagnosis descriptor 112 as an input and produces an output containing a plurality of prescriptive elements 136.

With continued reference to FIG. 2, prescriptive generator module 108 receives at least a diagnosis descriptor 112 from a user client device 116 wherein the at least a diagnosis descriptor 112 contains a current or future probable medical condition. At least a diagnosis descriptor 112 includes any of the diagnosis descriptor 112 as described above in reference to FIG. 1. At least a diagnosis descriptor 112 may include a current medical condition that a user may have been diagnosed with such as Celiac disease. In yet another non-limiting example at least a diagnosis descriptor 112 may include a current medical condition such as hairy cell leukemia. At least a diagnosis descriptor 112 may contain a future probable medical condition that a user may experience and/or be diagnosed with at some point in the future.

At least a diagnosis descriptor 112 may contain a future medical condition that a user may be at risk for due to the presence and/or absence of one or more risk factors for a particular medical condition. For instance and without limitation, at least a diagnosis descriptor 112 may contain a future medical condition such as heart disease due to the presence of risk factors for heart disease that a user exhibits including for example high blood pressure, high cholesterol and smoking. At least a diagnosis descriptor 112 may contain a future medical condition that a user may be at risk for due to a genetic predisposition such as by the absence of one or more alleles, single nucleotide polymorphism (SNPs) and the like. For instance and without limitation, at least a diagnosis descriptor 112 may contain a future medical condition such as Alzheimer's disease that a user may be at risk for developing later in life due to the presence of two copies of the apolipoprotein E 4 (APOE 4) gene. At least a diagnosis descriptor 112 may contain a future medical condition such as lactose intolerance that a user may develop at any time due to the presence of one gene mutation of the MCM6 gene that controls production of lactase enzyme that metabolizes lactose. Prescriptive generator module 108 may receive at least a diagnosis descriptor 112 from a user client device 116 utilizing any network topology as described herein. User client device 116 may include any of the user client device 116 as described above in reference to FIG. 1.

With continued reference to FIG. 2, user may be informed of at least a diagnosis descriptor 112 from a medical professional who may diagnose user as having a particular disease, condition, and/or future probable medical condition. Medical professional may include any licensed health professional who may be authorized by a medical licensing board to diagnose disease and/or conditions including for example, a medical doctor, a doctor of osteopathy, a nurse practitioner, a physician assistant, a doctor of optometry, a doctor of dental medicine, a doctor of dental surgery, a naturopathic doctor, a doctor of physical therapy, a nurse, a doctor of chiropractic medicine, a doctor of oriental medicine, and the like.

With continued reference to FIG. 2, prescriptive generator module 108 receives prescriptive training data 120 from a machine-learning database 124 correlating at least a diagnosis descriptor 112 to at least a prescriptive element. Prescriptive generator module 108 may receive prescriptive training data 120 containing at least a diagnosis descriptor 112 that matches diagnosis descriptor 112 received from a user client device 116. For instance and without limitation, prescriptive generator module 108 may receive prescriptive training data 120 correlating rheumatoid arthritis to at least a prescriptive element which may match a diagnosis descriptor 112 received from a client device containing rheumatoid arthritis. In yet another non-limiting example, prescriptive generator module 108 may receive prescriptive training data 120 correlating small intestinal bacterial overgrowth (SIBO) to at least a prescriptive element which may match a diagnosis descriptor 112 received from a client device containing SIBO. Prescriptive generator module 108 may receive at least a diagnosis descriptor 112 containing a disease classifier wherein the disease classifier includes a disease stage descriptor and receives prescriptive training data 120 from a machine-learning database 124 as a function of the at least a disease stage descriptor. Disease classifier may include any of the disease classifiers as described above in reference to FIG. 1. Disease classifier may indicate a particular body region and/or body system impacted by particular disease. For instance and without limitation, diagnosis descriptor 112 such as trigeminal neuralgia may contain a disease classifier that includes the mandibular area. In yet another non-limiting example, diagnosis descriptor 112 such as irritable bowel syndrome may contain a disease classifier that includes body system indicating the digestive system. Disease classifier includes a disease stage descriptor, which includes any of the disease stage descriptors as described above in reference to FIG. 1. Disease stage descriptor includes an indication describing the extent to which a particular disease has progressed. For instance and without limitation, diagnosis descriptor 112 such as Lyme Disease may include a stage two disease stage descriptor when two or more joints may be affected. In yet another non-limiting example, diagnosis descriptor 112 such as plaque psoriasis may include a stage one disease stage descriptor when skin rashes occur two or less times each year. In yet another non-limiting example, diagnosis descriptor 112 such as sickle cell disease may include a stage four disease stage descriptor when a user experiences painful swelling of hands and feet, frequent infections, delayed growth, vision problems, fever, abdominal swelling, and severe pain. In an embodiment, each individual diagnosis descriptor 112 containing a current or future probable medical condition may include its own individual staging criteria as described above in more detail in reference to FIG. 1. Prescriptive generator module 108 receives prescriptive training data 120 from machine-learning database 124 as a function of at least a disease stage descriptor. For instance and without limitation, prescriptive generator module 108 may receive prescriptive training data 120 correlating stage three rheumatoid arthritis to at least a prescriptive element which may match a diagnosis descriptor 112 containing a disease stage descriptor received from a client device containing stage three rheumatoid arthritis. In yet another non-limiting example, prescriptive generator module 108 may receive prescriptive training data 120 correlating stage one multiple sclerosis to at least a prescriptive element which may match a diagnosis descriptor 112 containing a disease stage descriptor received from a client device containing stage one multiple sclerosis. Machine-learning database 124 may contain tables organizing prescriptive training data 120 by disease type, disease classifier, and/or disease stage descriptor as described in more detail below.

With continued reference to FIG. 2, prescriptive generator module 108 may include a supervised machine-learning module 204 that may generate using a supervised machine-learning process a prescriptive model 132 that receives at least a diagnosis descriptor 112 as an input and produces an output containing a plurality of prescriptive elements 136. Supervised machine-learning module may include any hardware or software module. Supervised machine-learning process may include any of the supervised machine-learning processes as described above in reference to FIG. 1. Supervised machine-learning processes include algorithms that receive a training set relating a number of inputs to a number of outputs and seek to find one or more mathematical relations relating inputs to outputs, where each of the one or more mathematical relations is optimal according to some criterion specified to the algorithm using some scoring function. For instance, a supervised learning algorithm may use elements of diagnosis descriptor 112 data as inputs, prescriptive elements as outputs, and a scoring function representing a desired form of relationship to be detected between elements of diagnosis descriptor 112 data and prescriptive elements; scoring function may, for instance, seek to maximize the probability that a given element of diagnosis descriptor 112 data and/or combination of elements of diagnosis data is not associated with a given prescriptive element and/or combination of prescriptive elements. Scoring function may be expressed as a risk function representing an "expected loss" of an algorithm relating inputs to outputs, where loss is computed as an error function representing a degree to which a prediction generated by the relation is incorrect when compared to a given input-output pair provided in prescriptive training data 120. Persons skilled in the art, upon reviewing the entirety of this disclosure, will be aware of various possible variations of supervised machine-learning algorithms that may be used to determine relation between elements of diagnosis descriptor 112 data and prescriptive elements. In an embodiment, one or more supervised machine-learning algorithms may be restricted to a particular domain for instance, a supervised machine-learning process may be performed with respect to a given set of parameters and/or categories of parameters that have been suspected to be related to a given set of diagnosis descriptor 112, and/or are specified as linked to a medical specialty and/or field of medicine covering a particular set of diagnosis descriptor 112. As a non-limiting example, a particular set of treatments may be utilized by cardiologists to treat particular cardiac conditions and a supervised machine-learning process may be performed to relate cardiac conditions to particular treatments; in an embodiment, domain restrictions of supervised machine-learning procedures may improve accuracy of resulting models by ignoring artifacts in training data. Domain restrictions may be suggested by experts and/or deduced from known purposes for particular evaluations and/or known treatments for particular diseases and/or stages of disease. Additional supervised learning processes may be performed without domain restrictions to detect, for instance, previously unknown and/or unsuspected relationships between diagnosis descriptor 112 data and prescriptive elements.

With continued reference to FIG. 2, prescriptive generator module 108 produces an output containing a plurality of prescriptive elements 136. Prescriptive elements include any of the prescriptive elements as described above in reference to FIG. 1. Prescriptive generator module 108 generates a plurality of prescriptive elements 136 that may be utilized to treat current and/or future probable medical condition contained within diagnosis descriptor 112. For instance and without limitation, prescriptive generator module 108 may generate a plurality of prescriptive elements 136 for a current medical condition such as gout contained within at least a diagnosis descriptor 112 which include colchicine, low-purine diet, allopurinol, prednisone, celery juice, and/or cherry juice extract. In yet another non-limiting example, prescriptive generator module 108 generates a plurality of prescriptive elements 136 that may be utilized to treat a current medical condition such as systemic *Candida albicans* infection which may include fluconazole, ketoconazole, garlic extract, caprylic acid, grain-free diet, and/or sugar free diet.

With continued reference to FIG. 2, prescriptive generator module 108 is configured to select a prescriptive model 132 as a function of at least a diagnosis descriptor 112. In an embodiment, prescriptive model 132 may have been previously generated and loaded within system 100. Prescriptive model 132 may be organized and stored by category of diagnosis descriptor 112 as described in more detail below. In an embodiment, prescriptive generator module 108 selects a prescriptive model 132 containing a diagnosis descriptor 112 that matches at least a diagnosis descriptor 112 received from a user client device 116. For example, prescriptive generator module 108 may select a prescriptive model 132 that contains prescriptive elements for a diagnosis descriptor 112 such as Cushing's disease after receiving at least a diagnosis descriptor 112 from a user client device 116 that contains Cushing's disease. In an embodiment, selecting a prescriptive model may be performed utilizing machine-learning whereby prescriptive generator module may select a prescriptive model by learning which prescriptive model to select for a particular diagnosis descriptor.

Figure 3:
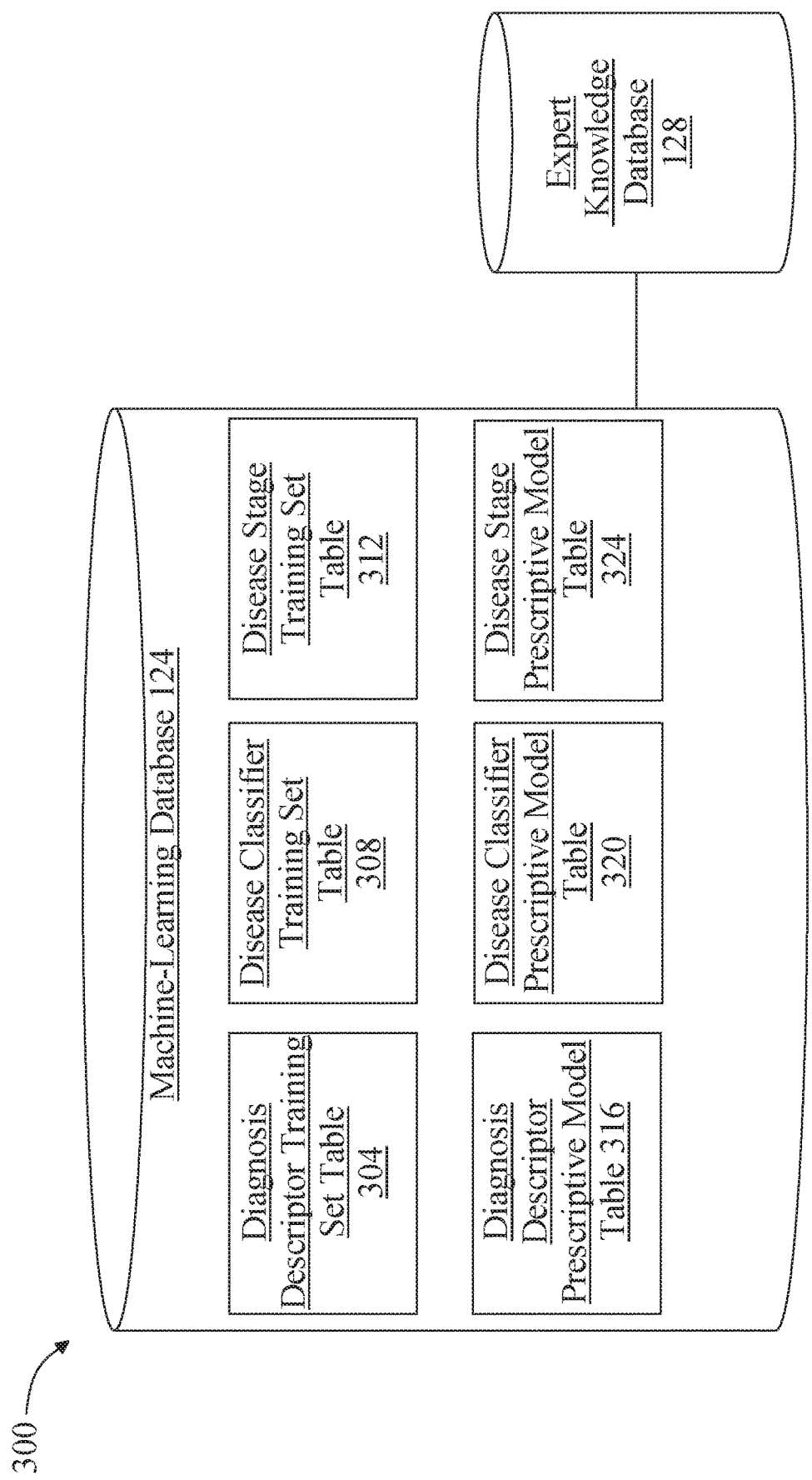
FIG. 3 is a block diagram illustrating an exemplary embodiment of a machine-learning database.

Referring now to FIG. 3, an exemplary embodiment 300 of machine-learning database 124 is illustrated. Machine-learning database 124 may organize data stored in machine-learning database 124 according to one or more database tables. One or more database tables may be linked to one another by, for instance, common column values. For instance, a common column between two tables may include an identifier of a diagnosis descriptor 112 which may be linked to a disease classifier. Persons skilled in the art, upon reviewing the entirety of this disclosure, will be ware of various ways in which one or more database tables may be linked to one another.

With continued reference to FIG. 3, one or more tables contained within machine-learning database 124 may include diagnosis descriptor training set table 304; diagnosis descriptor training set table 304 may include one or more entries containing prescriptive training sets organized by diagnosis descriptor 112. For instance and without limitation, diagnosis descriptor training set table 304 may include a first entry containing a prescriptive training set organized by diagnosis descriptor 112 such as rheumatoid arthritis and a second entry containing a prescriptive training set organized by diagnosis descriptor 112 such as Lupus. One or more tables contained within machine-learning database 124 may include disease classifier training set table 308; disease classifier training set table 308 may include one or more entries containing prescriptive training sets organized by disease classifiers. For instance and without limitation, disease classifier training set table 308 may include a first entry containing a prescriptive training set pertaining to rheumatoid arthritis located on proximal interphalangeal joint and a second entry containing a prescriptive training set pertaining to dermatitis herpetiformis affecting the left elbow. One or more tables contained within machine-learning database 124 may include disease stage training set table 312; disease stage training set table 312 may include one or more entries containing prescriptive training sets organized by disease stage classifiers. For instance and without limitation, disease stage training set table 312 may include a first entry containing a prescriptive training set pertaining to stage two lupus and a second entry containing a prescriptive training set pertaining to stage one non-Hodgkin's lymphoma. One or more tables contained within machine-learning database 124 may include diagnosis descriptor prescriptive model table 316; diagnosis descriptor prescriptive model table 316 may include one or more entries containing prescriptive model 132 organized by diagnosis descriptor 112. For instance and without limitation, diagnosis descriptor prescriptive model table 316 may include a first entry containing a prescriptive model 132 for tendonitis and a second entry containing a prescriptive model 132 for frozen shoulder. One or more tables contained within machine-learning database 124 may include disease classifier prescriptive model table 320; disease classifier prescriptive model table 320 may include one or more entries containing prescriptive model 132 organized by disease classifier prescriptive model 132. For instance and without limitation, disease classifier prescriptive model table 320 may include a first entry containing a prescriptive model 132 for a bone bruise located on the talocrural joint and a second entry containing a prescriptive model 132 for osteoarthritis located at the interphalangeal joint of the third finger. One or more tables contained within machine-learning database 124 may include disease stage prescriptive model table 324; disease stage prescriptive model table 324 may include one or more entries containing prescriptive model 132 organized by disease stage. For instance and without limitation, disease stage prescriptive model table 324 may include a first entry containing a prescriptive model 132 for stage four back pain and a second entry containing a prescriptive model 132 for stage one urinary tract infection. Entries organized and/or maintained within machine-learning database 124 may be received from expert knowledge database 128 as described in more detail below.

Figure 4:
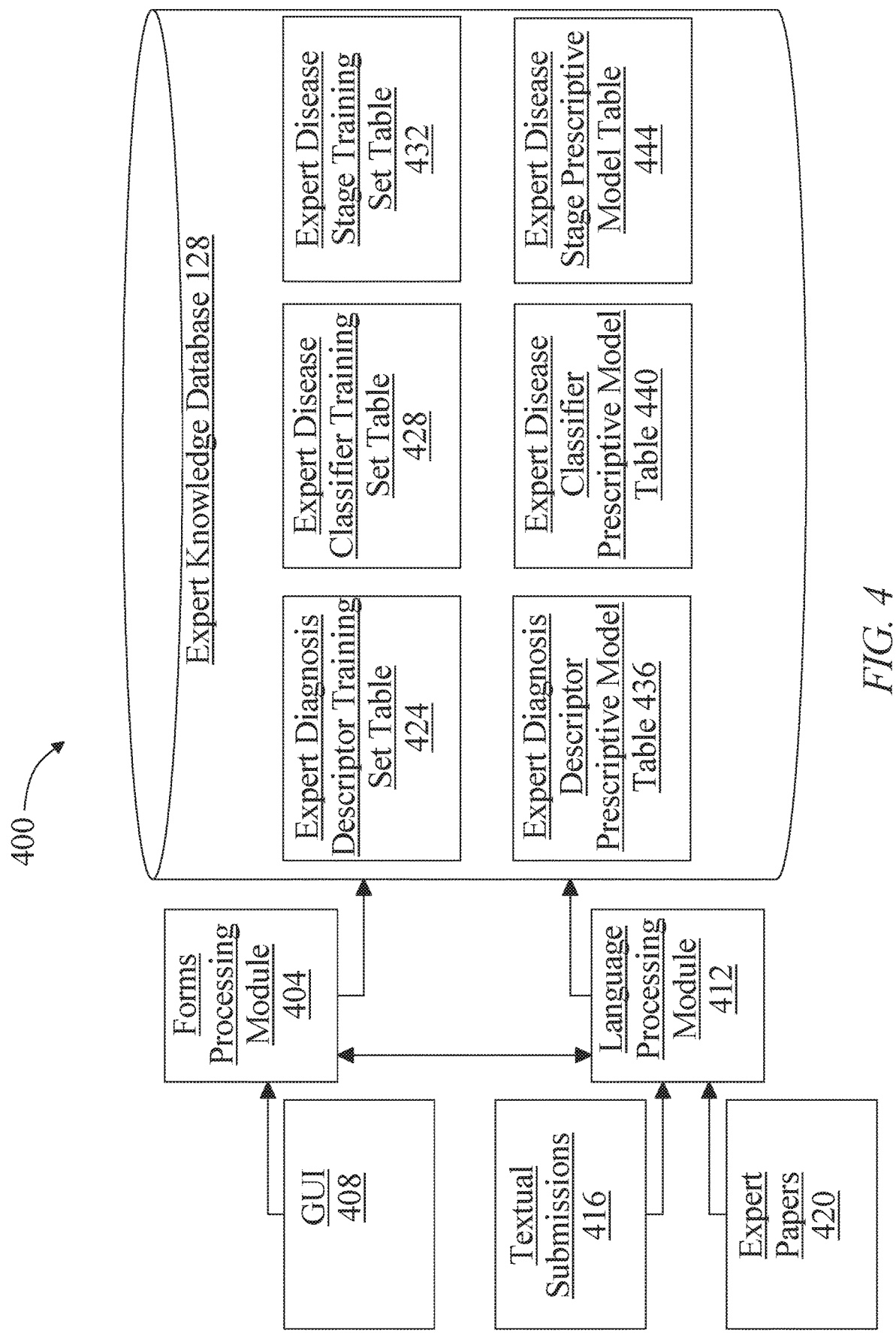
FIG. 4 is a block diagram illustrating an exemplary embodiment of an expert knowledge database.

Referring now to FIG. 4, an exemplary embodiment 400 of expert knowledge database 128 is illustrated. Expert knowledge database 128 may include any data structure for ordered storage and retrieval of data, which may be implemented as a hardware or software module, and which may be implemented as any database structure suitable for use as machine-learning database 124. Expert knowledge database 128 includes a forms processing module 404 that may sort data entered in a submission via graphical user interface 408 by, for instance, sorting data from entries in the first graphical user interface 408 to related categories of data; for instance, data entered in an entry relating in the graphical user interface 408 to a training data set may be sorted into variables and/or data structures for storage of training data sets, while data entered in an entry relating to a prescriptive model 132 may be sorted into variables and/or data structures for the storage of, respectively, categories of prescriptive model 132 data. Where data is chosen by an expert from pre-selected entries such as drop-down lists, data may be stored directly; where data is entered in textual form, language processing module 412 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 412 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 416, such as accomplished by filling out a paper or PDF form and/or submitting narrative information, may likewise be processed using language processing module 412. Data may be extracted from expert papers 420, which may include without limitation publications in medical and/or scientific journals, by language processing module 412 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 4, one or more tables contained within expert knowledge database 128 may include expert diagnosis descriptor training set table 424; expert diagnosis descriptor training set table 424 may include any information provided by one or more experts regarding diagnosis descriptor 112 prescriptive training sets. One or more tables contained within expert knowledge database 128 may include expert disease classifier training set table 428; expert disease classifier training set table 428 may include any information provided by one or more experts regarding disease classifier prescriptive training sets. One or more tables contained within expert knowledge database 128 may include expert disease stage prescriptive training set table 432; expert disease stage training set table 432 may include any information provided by one or more experts regarding disease stage prescriptive training sets. One or more tables contained within expert knowledge database 128 may include expert diagnosis descriptor prescriptive model table 436; expert diagnosis descriptor prescriptive model table 436 may include any information provided by one or more experts regarding diagnosis descriptors and/or prescriptive models. One or more tables contained within expert knowledge database 128 may include expert disease classifier prescriptive model table 440; expert disease classifier prescriptive model table 440 may include any information provided by one or more experts regarding expert disease classifier prescriptive model 132. One or more tables contained within expert knowledge database 128 may include expert disease stage prescriptive model table 444; expert disease stage prescriptive model table 444 may include any information provided by one or more experts regarding expert disease stage prescriptive model 132.

Figure 5:
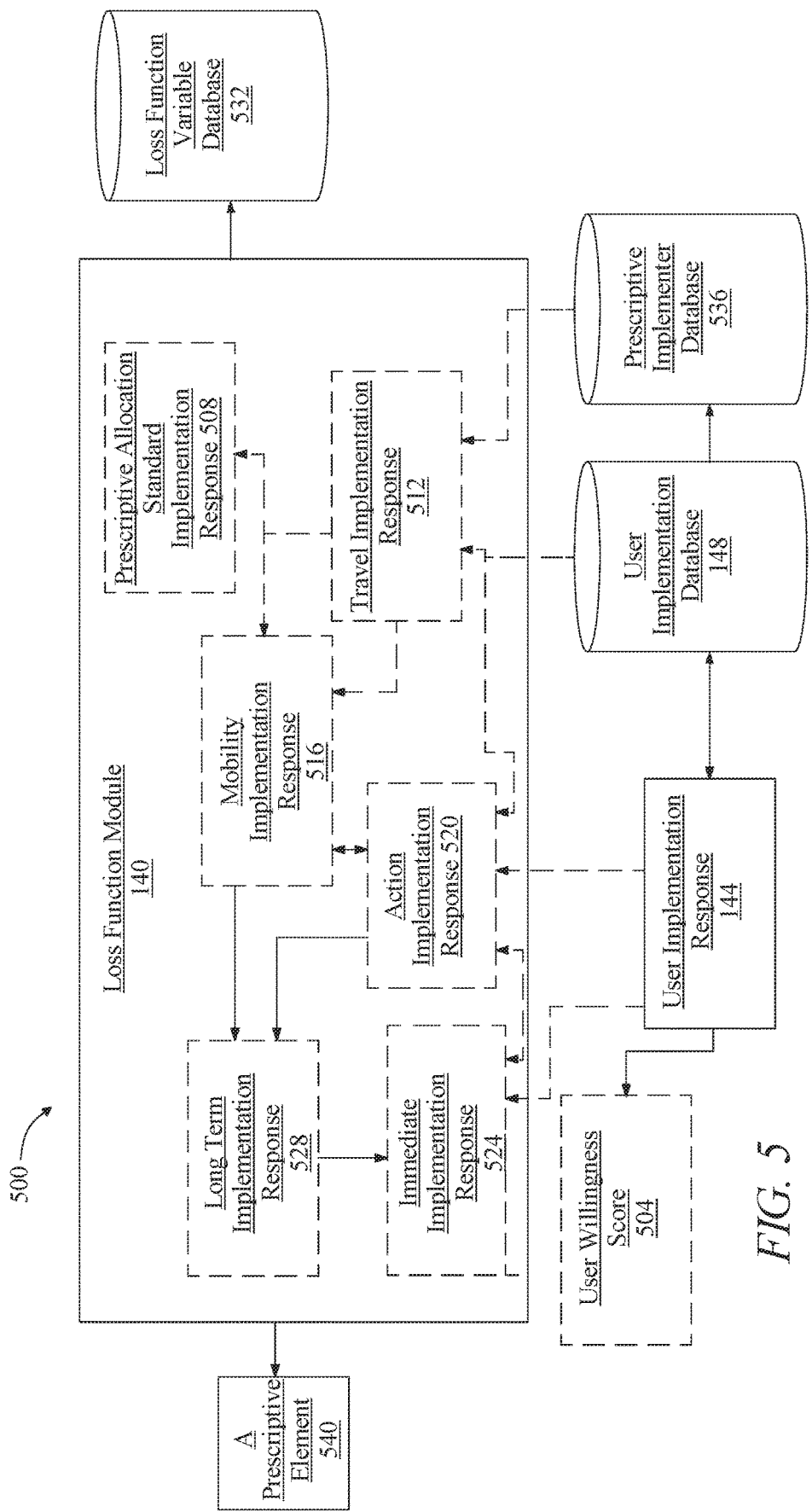
FIG. 5 is a block diagram illustrating an exemplary embodiment of a loss function module.

Referring now to FIG. 5, an exemplary embodiment 500 of loss function module 140 is illustrated. Loss function module 140 may be implemented as a hardware or software module. Loss function module 140 is configured to receive from a user client device 116 at least a user implementation response 144 wherein the at least a user implementation response 144 contains at least a prescriptive element indicator; receive the at least a diagnosis descriptor 112 and the plurality of prescriptive elements 136 from the prescriptive generator module 108; generate a loss function as a function of the at least a user implementation response 144 and the plurality of prescriptive elements 136; minimize the loss function; select a prescriptive element as a function of minimizing the loss function; and transmit the selected prescriptive element to the user client device 116.

With continued reference to FIG. 5, loss function module 140 receives from a user client device 116 at least a user implementation response 144, which may be received utilizing any network topology as described herein. At least a user implementation response 144 includes data describing a user's response towards one or more parameters necessary to implement prescriptive element as described in more detail above in reference to FIG. 1. Implementing prescriptive element includes performing to and/or adhering to a prescriptive element. For instance and without limitation, implementing prescriptive element such as performing a yoga sequence for thirty minutes a total of five times each week may include practicing and performing the yoga sequence for thirty minutes for at least five times each week. In yet another non-limiting example, implementing prescriptive element such as taking a medication by mouth twice per day to treat multiple sclerosis may include swallowing the pill two times per day by mouth for the prescribed course of treatment. At least a user implementation response 144 may include a user willingness score 504 containing a user effort factor. User willingness score includes an element of data describing a user's willingness to partake in a particular prescriptive element as described in more detail above in reference to FIG. 1. User willingness score may indicate how motivated a user may be to partake in and adhere to a particular prescriptive element. In an embodiment, user willingness score may include a user effort factor. A "user effort factor" as used in this disclosure contains a numerical response that indicates how much effort a user is willing to devote to a particular prescriptive element. Effort may include an indication of how likely it is that a user may shop for groceries for a particular prescriptive element or adhere to a particular supplement regimen. For instance and without limitation, user willingness score may include a user effort factor that indicates a user is not willing to put much effort into a prescriptive element such as yoga, but the user is willing to put effort into a prescriptive element such as practicing a meditation sequence.

With continued reference to FIG. 5, user implementation response 144 may be stored and maintained in user implementation database 148. Loss function module 140 may utilize user implementation response 144 receive from user client device 116 and/or user implementation database 148 to generate loss function. User implementation database 148 may store user entries as described in more detail below. User implementation response 144 may include prescriptive allocation standard implementation response 508 which may contain a description of the total amount of resources that a user is willing to devote to a prescriptive element as described above in more detail in reference to FIG. 1. For instance and without limitation, prescriptive allocation standard implementation response 508 may include data describing the total amount of money that a user is willing to spend on any given prescriptive element for a certain amount of time such as for the course of one year. In yet another non-limiting example, prescriptive allocation standard implementation response 508 may include data describing the total percentage of a user's salary that a user is willing to spend on any given prescriptive element for a period of three months. User implementation response 144 may include travel implementation response 512. Travel implementation response 512 may include data describing how far a user is willing to travel for a particular prescriptive element. For instance and without limitation, a user may enter a travel implementation response 512 that contains data indicating that a user is willing to travel twenty five meals for any treatment contained within a particular prescriptive element. In yet another non-limiting example, travel implementation response may include data regarding a user who lives in Louisiana who is willing to travel to Arkansas and Texas for a prescriptive element but not to Georgia. User implementation response 144 may include mobility implementation response 516. Mobility implementation response 516 may include information describing a user's mobility to partake in and travel for prescriptive elements. For instance and without limitation, mobility implementation response 516 may include information describing a user's ability to partake in group exercise class at a gym or if exercise at home with the help of a fitness coach may be better suited.

User implementation response 144 may include action implementation response 520. Action implementation response 520 may include information describing how difficult a particular prescriptive element may be for a user to implement and/or take action on. For instance and without limitation, action implementation response 520 may include information describing partaking in a spinning class three days each week may be difficult for a user to implement and perform while taking a pill by mouth three times each day may be easier for a user to implement. User implementation response 144 may include immediate implementation response 524. Immediate implementation response 524 may include information describing how immediate a user seeks to implement a particular prescriptive element and immediately experience results. For example, immediate implementation response 524 may include data describing a user who is not in a rush to implement a prescriptive element and does not seek to achieve immediate results. User implementation response 144 may include long term implementation response 528. Long term implementation response 528 may include information describing results a user seeks to obtain over the long-term future. For example, long term implementation response 528 may include data describing a user who seeks to obtain results from a particular prescriptive element over the long term. User implementation response 144 may include other responses not illustrated in FIG. 5. For example, user implementation response 144 may indicate how willing a user is looking to reverse a root cause of user's illness and achieve vibrant health and longevity.

With continued reference to FIG. 5, loss function module 140 receives at least a diagnosis descriptor 112 and a plurality of prescriptive elements 136 from prescriptive generator module 108 and generates a loss function as a function of at least a user implementation response 144 and the plurality of prescriptive elements 136. Loss function module 140 generates a loss function utilizing any of the methodologies as described above in reference to FIG. 1. Loss function module 140 generates loss function by evaluating at least a user implementation response 144 to obtain a user implementation factor where the user implementation factor contains a numerical scored response. User implementation factor may reflect the importance of a user implementation response 144 as compared to other user implementation response 144. For instance and without limitation, a user who has limited mobility and is unable to operate a motor vehicle may enter a user implementation factor for travel implementation response 512 as being highly important while immediate implementation response 520 is of little importance to user. In yet another non-limiting example, a user who lives on a fixed income may enter a user implementation factor for prescriptive allocation standard implementation response 508 as being having a high user implementation factor and being of great importance to the user while a user implementation factor for mobility implementation response 516 may contain a lower user implementation factor indicating it is of little importance to the user. In generating a loss function, loss function module 140 assigns a weighted variable to at least a user implementation response 144 as a function of a user implementation factor and minimizes the loss function as a function of the weighted variable. Variables assigned to at least a user implementation response 144 140 may be contained within loss function variable database 532. Loss function module 140 may utilize user implementation factor to look up and/or calculate a variable contained within loss function variable database. In an embodiment, variables may be assigned to at least a user implementation response 144 based on previous interactions of a user with system 100 and previous user behaviors which may be stored within user implementation database 148.

With continued reference to FIG. 5, loss function module 140 classifies at least a user implementation response 144 as a function of a user implementation factor. Classifications may include any of the classifications as described above in reference to FIG. 1. Classification label may include data describing which category a particular user implementation response 144 belongs to. Categories may include any of the categories as described above in reference to FIG. 1, including optimal, average, and low. In an embodiment, user implementation factors that contain low scores indicating user implementation factors of little importance may be classified as low while user implementation factors that contain high scores indicating user implementation factors of high importance may be classified as optimal. Loss function module 140 generates classification labels as a function of classifying at least a user implementation response 144. Loss function module 140 selects at least a user implementation response 144 containing an "optimal" classification label and minimizes the total variance from the at least a user implementation response 144 containing an optimal classification label. For instance and without limitation, loss function module 140 may select action implementation response for a user containing an optimal classification label and minimize the total variance from the action implementation response.

With continued reference to FIG. 5, loss function module 140 generates a plurality of user implementation neutralizers. User implementation neutralizers may include any of the user implementation neutralizers as described above in reference to FIG. 1. Loss function module 140 may generate user implementation neutralizers by selecting user implementation response 144 that contain a low weighted variable score and/or are classified as containing a "low" and/or "average" classification labels. Loss function module 140 transmits the plurality of user implementation neutralizers to user client device 116. This may be performed utilizing any network topography as described herein. Loss function module 140 receives a user implementation neutralizer response from user client device 116. User implementation neutralizer response may contain a selection of a user implementation neutralizer from the plurality of user implementation neutralizers. Loss function module 140 selects a user implementation neutralizer as a function of the user implementation neutralizer response and minimizes the loss function utilizing the selected user implementation neutralizer.

With continued reference to FIG. 5, loss function module 140 includes prescriptive implementer database 536. Prescriptive implementer database may include data entries that may aid in selecting a prescriptive element and minimizing the loss function as described in more detail below.

Figure 6:
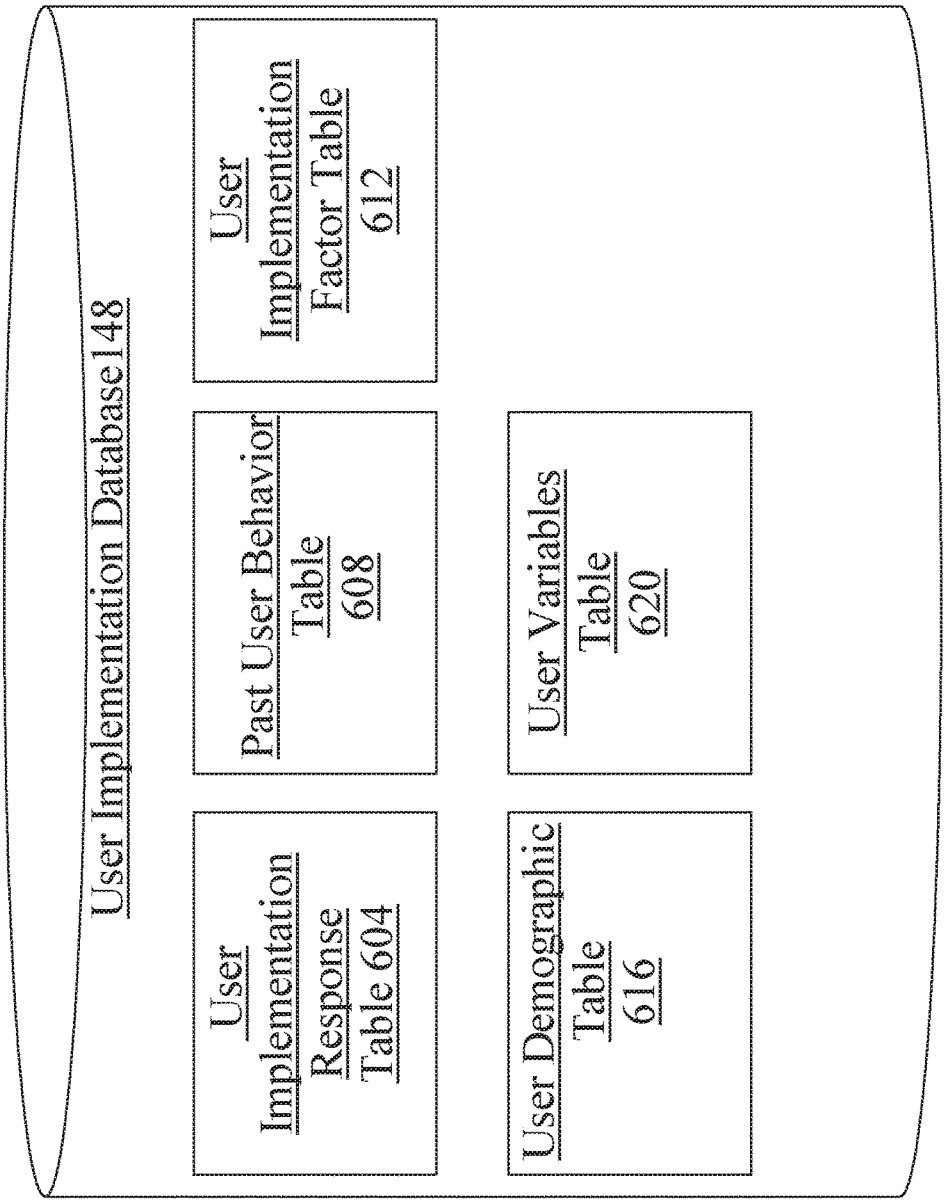
FIG. 6 is a block diagram illustrating an exemplary embodiment of a user implementation database.

Referring now to FIG. 6, an exemplary embodiment 600 of user implementation database 148 is illustrated. User implementation database 148 may include any data structure for ordered storage and retrieval of data, which may be implemented as a hardware or software module, and which may be implemented as any database structure suitable for use as machine-learning database 124. One or more tables contained within user implementation database 148 may include user implementation response 144 table 604; user implementation response 144 table 604 may include data entries containing one or more stored user implementation response 144. For instance and without limitation, user implementation response 144 table 604 may include a user implementation response 144 such as mobility implementation response 516 and long term implementation response 528. One or more tables contained within user implementation database 148 may include past user behavior table 608; past user behavior table 608 may include data entries describing one or more past user behaviors. For instance and without limitation, past user behavior table 608 may include data entries describing past user behaviors such as how far a user traveled to have an appointment with a medical doctor or how much money a user spent on a particular prescriptive element such as a supplement or nutraceutical. One or more tables contained within user implementation database 148 may include user implementation factor table 612; user implementation factor table 612 may include one or more data entries containing one or more user implementation factor responses. For instance and without limitation, user implementation factor table 612 may include one or more user data entries containing a user implementation factor for a particular user implementation response 144 such as action implementation response 520. One or more tables contained within user implementation database 148 such as action implementation response 520. One or more tables contained within user implementation database 148 may include user demographic table 616; user demographic table 616 may include one or more data entries describing user demographic information. For instance and without limitation, user demographic table 616 may include user contact information, home address, allergies, payment information, marital status, household income, occupation, age, gender, and the like. One or more tables contained within user implementation database 148 may include user variables table 620; user variables table 620 may include one or more weighted variables that may be assigned to a user implementation response 144. For instance and without limitation, user variables table 620 may include one or more weighted variables assigned to at least a user implementation response 144 such as mobility implementation response 516 utilized by loss function module 140 to calculate and minimize the loss function.

Figure 7:
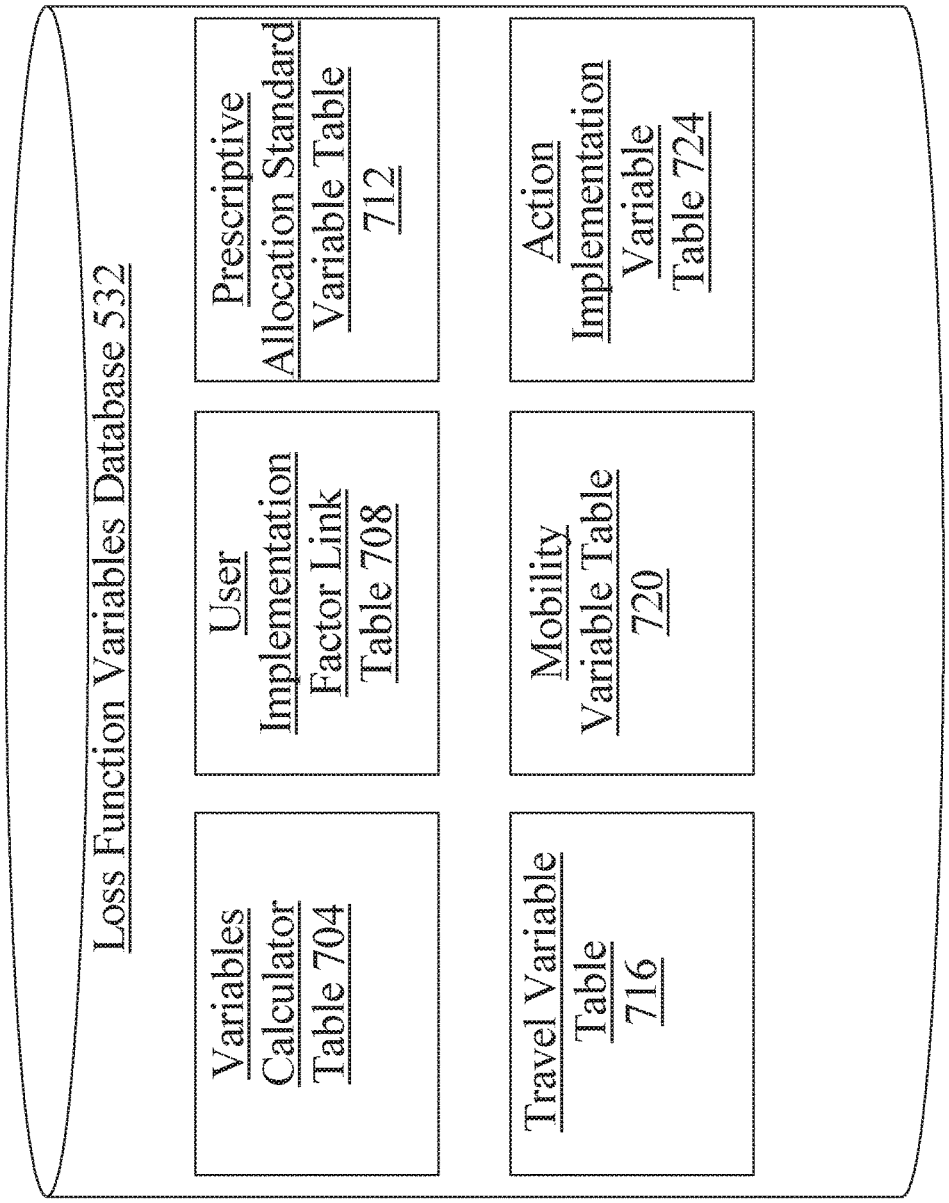
FIG. 7 is a block diagram illustrating an exemplary embodiment of a loss function variables database.

Referring now to FIG. 7, an exemplary embodiment 700 of loss function variables database 532 is illustrated. Loss function variables database 532 may include any data structure for ordered storage and retrieval of data, which may be implemented as a hardware or software module, and which may be implemented as any database structure suitable for use as machine-learning database 124. One or more tables contained within loss function variables database 532 may include variables calculator table 704; variables calculator table 704 may include one or more calculations and/or algorithms utilized to calculate loss function variables. One or more tables contained within loss function variables database 532 may include user implementation factor link table 708; user implementation factor link table 708 may include one or more entries linking user implementation factors contained within user implementation database 148 and utilized to calculate variables. One or more tables contained within loss function variables database 532 may include prescriptive allocation standard variable table 712; prescriptive allocation standard variable table 712 may include variables for prescriptive allocation standard user implementation response 144. One or more tables contained within loss function variables database 532 may include travel variable table 716; travel variable table 716 may include variables for travel user implementation response 144. One or more tables contained within loss function variables database 532 may include mobility variable table 720; mobility carriable table 720 may include variables for mobility user implementation response 144. One or more tables contained within loss function variables database 532 may include action implementation variable table 724; action implementation variable table 724 may include variables for action user implementation response 144.

Figure 8:
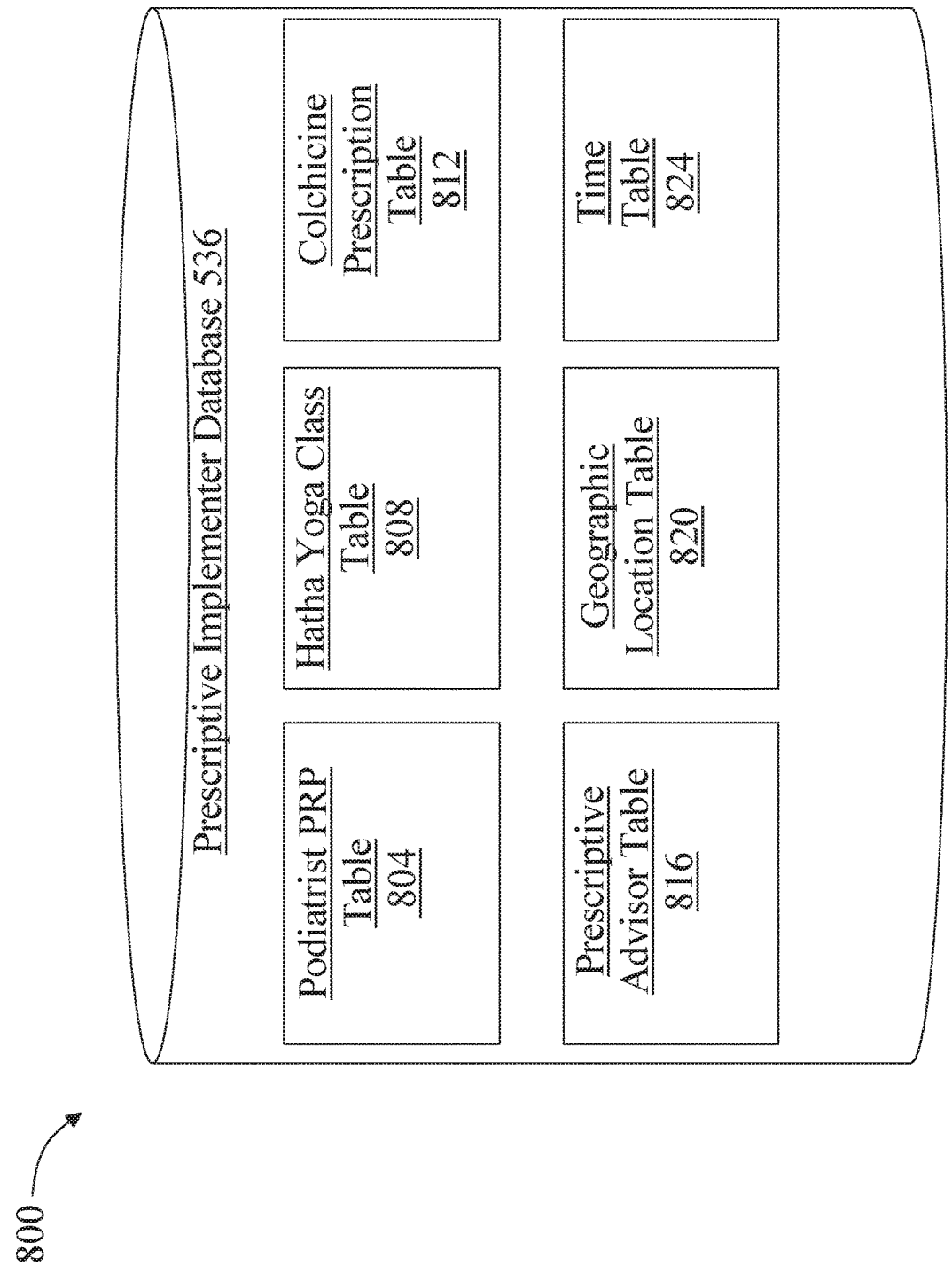
FIG. 8 is a block diagram illustrating an exemplary embodiment of a prescriptive implementer database.

Referring now to FIG. 8, an exemplary embodiment 800 of prescriptive implementer database 536 is illustrated. Prescriptive implementer database 536 may include any data structure for ordered storage and retrieval of data, which may be implemented as a hardware or software module, and which may be implemented as any database structure suitable for use as machine-learning database 124. Prescriptive implementer database 536 may include one or more data entries that may be utilized by loss function module 140 when minimizing loss function and selecting a prescriptive element. Prescriptive implementer database 536 may include one or more data entries including specific information that may be utilized to implement a particular prescriptive element. One or more tables contained within prescriptive implementer database 536 may include podiatrist PRP table 804; podiatrist PRP table 804 may include data entries describing information regarding podiatrist platelet rich plasma prescriptive elements. For instance and without limitation, podiatrist PRP table 804 may include information such as podiatrists within user's requested geographical location who may offer PRP injections, as well as costs associated with PRP injections, podiatrist availability for PRP injections, and the like. One or more tables contained within prescriptive implementer database 536 may include hatha yoga class table 808; hatha yoga class table 808 may include data entries describing information regarding hatha yoga class prescriptive elements. For instance and without limitation, hatha yoga class table 808 may include information such as available hatha yoga classes available within user's requested geographical location who may offer hatha yoga classes, costs of different hatha yoga classes, available times for hatha yoga classes, availability for hatha yoga classes to be offered at user's home residence, as well as equipment that may be necessary for hatha yoga classes. One or more tables contained within prescriptive implementer database 536 may include colchicine prescription table 812; colchicine prescription table 812 may include data entries describing information regarding colchicine prescriptive elements. For instance and without limitation, colchicine prescription table 812 may include data entries describing price for colchicine prescriptions available at pharmacies located within user's specified geographical location, as well as availability of pharmacies to have colchicine in stock, as well as delivery options for prescriptions such as if the user needs to have mobility to go into the pharmacy and pick up the colchicine prescription, or if the colchicine may be delivered to the user or shipped to the user. One or more tables contained within prescriptive implementer database 536 may include prescriptive advisor table 816; prescriptive advisor table 816 may include information about prescriptive advisors such as medical professionals who may be able to offer prescriptive elements for a user. For instance and without limitation, prescriptive advisor table 816 may include information describing particular medical professionals who may be able to prescribe a prescriptive element for a user. Prescriptive advisor table 816 may include information regarding prescriptive advisors who may be located within a user's preferred geographical location. One or more tables contained within prescriptive implementer database 536 may include geographic location table 820; geographical location table 820 may include information describing user's preferred geographic location. One or more tables contained within prescriptive implementer database 536 may include timetable 824; timetable 824 may include information describing user's time availability and/or preferred appointment times to meet with a medical professional and/or preferred time for a particular prescriptive element.

Figure 9:
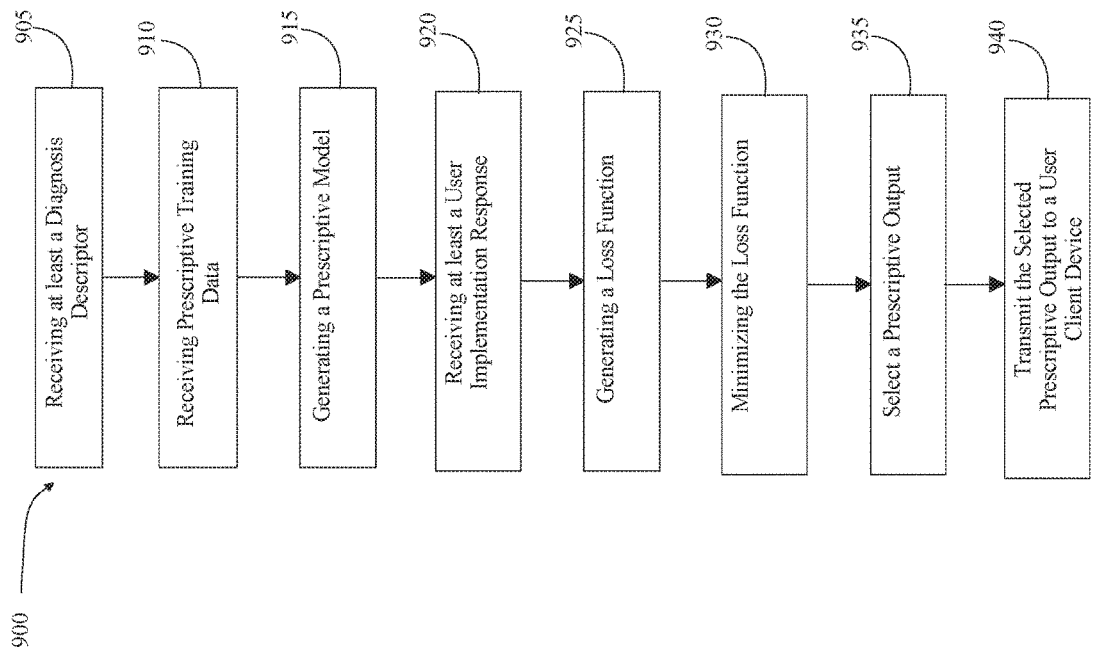
FIG. 9 is a process flow diagram illustrating an exemplary embodiment of a method of selecting a prescriptive element based on user implementation inputs.

Referring now to FIG. 9, an exemplary embodiment of a method 900 of selecting a prescriptive element based on user implementation inputs is illustrated. At step 905 at least a computing device receives at least a diagnosis descriptor 112 from a user client device 116 wherein the at least a diagnosis descriptor 112 contains a current or future probable medical condition. Computing device may include any of the computing devices as described herein. At least a diagnosis descriptor 112 may include any of the diagnosis descriptor 112 as described above in reference to FIGS. 1-9. In an embodiment, at least a diagnosis descriptor 112 may include a current medical condition a user has been diagnosed with by a medical professional such as rheumatoid arthritis. In an embodiment, at least a diagnosis descriptor 112 may include a future medical condition a user may be diagnosed with in the future such as a risk for developing Type 2 diabetes mellitus. At least a diagnosis descriptor 112 may be received by at least a computing device using any network topography as described herein. At least a diagnosis descriptor 112 may be generated by a user at a user client device 116. User client device 116 may include any of the user client device 116 as described above in reference to FIG. 1.

With continued reference to FIG. 9, at step 910 at least a computing device receives prescriptive training data 120 from a machine-learning database 124 correlating at least a diagnosis descriptor 112 to at least a prescriptive element. Prescriptive training data 120 may include any of the prescriptive training data 120 as described above in reference to FIGS. 1-9. Prescriptive training data 120 includes at least a diagnosis descriptor 112 correlated to at least a prescriptive element. Prescriptive element may include any of the prescriptive elements as described above in reference to FIGS. 1-9. For instance and without limitation, prescriptive training data 120 may include a diagnosis descriptor 112 such as osteoarthritis correlated to at least a prescriptive element such as acetaminophen 600 mg three times daily for twenty eight days. In yet another non-limiting example, prescriptive training data 120 may include a diagnosis descriptor 112 such as hypertriglyceridemia correlated to at least a prescriptive element such as fish oil 1000 mg twice daily for six months. In an embodiment, prescriptive training data 120 may be stored in machine-learning database 124 as described above in more detail in reference to FIG. 3. Prescriptive training data 120 may be stored within machine-learning database 124 according to type of diagnosis descriptor 112 contained within a particular prescriptive training data 120 set, as well as by disease classifier, and/or disease stage as described above in more detail in reference to FIG. 3.

With continued reference to FIG. 9, at least a computing device is configured to receive at least a diagnostic descriptor containing a disease classifier wherein the disease classifier includes a disease stage descriptor and receive prescriptive training data 120 from machine-learning database 124 as a function of at least a disease stage descriptor. Disease classifier may include any disease classifier as described above in reference to FIGS. 1-9. Disease stage descriptor may include any of the disease stage descriptors as described above in reference to FIGS. 1-9. In an embodiment, at least a computing device may receive prescriptive training data 120 from machine-learning database 124 by matching disease classifier and/or disease stage descriptor to a prescriptive training set contained within machine-learning database 124 organized and containing the same disease classifier and/or disease stage descriptor. For instance and without limitation, at least a diagnostic descriptor such as stage two polycystic ovarian syndrome may be matched to a prescriptive training set contained within machine-learning database 124 that includes disease stage descriptors containing stage two polycystic ovarian syndrome correlated to prescriptive elements.

With continued reference to FIG. 9, at step 915 at least a computing device generates using a supervised machine-learning process a prescriptive model 132 that receives at least a diagnosis descriptor 112 as an input and produces an output containing a plurality of prescriptive elements 136. Supervised machine-learning process may include any of the supervised machine-learning processes as described above in reference to FIGS. 1-9. At least a computing device is configured to select a prescriptive model 132 from a machine-learning database 124 as a function of at least a diagnostic descriptor. For instance and without limitation, at least a computing device may receive at least a diagnostic descriptor containing a current medical condition of hypothyroidism which may be utilized to select a prescriptive model 132 for hypothyroidism. In an embodiment, prescriptive model 132 may be organized according to diagnostic descriptor as described above in more detail in reference to FIG. 3. In an embodiment, prescriptive model 132 may be pre-generated and may be ready to produce outputs upon selection from machine-learning database 124 as described above in more detail in reference to FIG. 3. Prescriptive generator module transmits the plurality of prescriptive elements to a user client device wherein the plurality of prescriptive elements each contain a prescriptive allocation resource calculation. Prescriptive allocation resource calculation includes any of the prescriptive allocation resource calculations as described above in reference to FIG. 1. Transmitting the plurality of prescriptive allocation resource calculations enable a user to view treatment options that are most accessible to a user's current situation and ensure treatment is appropriate and will not create financial disaster. Transmitting the plurality of prescriptive allocation resource calculations linked to each prescriptive element helps a user to make an informed decision and evaluate the thoroughness of a medical professional who may be treating a user. Ultimately, this may help create greater transparency and trust between a user, medical professional, and an insurance company.

With continued reference to FIG. 9, at step 920 at least a computing device receives from a user client device 116 at least a user implementation response 144 wherein the at least a user implementation response 144 contains at least a prescriptive element indicator. At least a user implementation response 144 may include any of the user implementation response 144 as described above in reference to FIGS. 1-9. In an embodiment, at least a user implementation response 144 may include a travel implementation response, a mobility implementation response, an action implementation response and the like as described above in more detail in reference to FIG. 1 and FIG. 5. User implementation response 144 may include a prescriptive allocation standard response. Prescriptive allocation standard response may include a cost response indicating how many resources a user may be willing to allocate to a particular prescriptive element as described above in more detail in FIGS. 1-9. Prescriptive allocation standard response may include a treatment stage factor multiplied by a treatment length factor and a treatment accessibility factor as described in more detail above in reference to FIG. 1. For instance and without limitation, total amount of resources that a user may be willing to allocate to a prescriptive allocation standard response may be calculated to include factors based on how long a particular prescriptive element will be needed for multiplied by how accessible a particular prescriptive element is for a user. User implementation response 144 may include a numerical response reflecting a user willingness score wherein the user willingness score contains a user effort factor. User willingness score may include any of the user willingness scores as described above in reference to FIGS. 1-9. User effort factor may include any of the user effort factors as described above in reference to FIGS. 1-9. For instance and without limitation, user willingness score with a higher numerical response may indicate a user having more willingness to partake in a particular prescriptive element such as a meditation sequence as compared to a user willingness score with a lower numerical response which may indicate a user having less willingness to partake in a particular prescriptive element such as cardiovascular exercise three days each week.

With continued reference to FIG. 9, at step 925 at least a computing device generates a loss function as a function of at least a user implementation response 144 and a plurality of prescriptive elements 136. Computing device generates loss function utilizing any of the methods as described above in reference to FIGS. 1-10. Generating a loss function includes evaluating at least a user implementation response 144 to obtain a user implementation factor wherein the user implementation factor contains a numerical scored response, assigning a weighted variable to at least a user implementation response 144 as a function of the user implementation factor and minimize the loss function as a function of the weighted variable. Variables may be calculated and stored within loss function variables database as described above in more detail in reference to FIG. 7. Generating a loss function includes classifying at least a user implementation response 144 as a function of a user implementation factor. User implementation response 144 containing high numerical scored responses may be classified as optimal indicating that a particular user implementation response 144 is of high importance to a user as described above in more detail. User implementation response 144 containing low numerical scored responses may be classified as low indicating that a particular user implementation response 144 is of low importance to a user. User implementation response 144 containing average numerical scored responses may be classified as average. User implementation response 144 classified as low and/or average may contain low variables scores and/or weights may be utilized to minimize user implementation response 144 that contain high variables scores and/or weights as described in more detail below.

With continued reference to FIG. 9, at step 930 at least a computing device minimizes the loss function. At least a computing device may minimize the loss function by selecting a user implementation response 144 having a small variable that may minimize the loss function. Identification of user implementation response 144 having small variables may be done by identifying user implementation neutralizes. At least a computing device may generate a plurality of user implementation neutralizers. User implementation neutralizers may include any of the user implementation neutralizers as described above in reference to FIGS. 1-9. In an embodiment, user implementation neutralizers may include user implementation response 144 containing user implementation factors that contain low numerical scored responses and may contain a classification label of low or average. At least a computing device transmits the plurality of user implementation neutralizers to a user client device 116. This may be performed utilizing any network topography as described herein. At least a computing device receives a user implementation neutralizer response from a user client device 116. User implementation neutralizer response may indicate which of the plurality of user implementation neutralizers may be of least important to user. In an embodiment, at least a computing device may transmit the plurality of user implementation neutralizers to a user client device 116 in ranked descending order of largest variable to smallest variable. At least a computing device selects a user implementation neutralizer as a function of the user implementation neutralizer response and minimizes the loss function utilizing the selected user implementation neutralizer. At least a computing device may utilize the selected user implementation neutralizer containing a small value variable to minimize a user implementation response 144 containing a large variable or weight. User implementation response 144 containing large variables or weight may be classified to contain optimal classification labels.

With continued reference to FIG. 9, at step 935 at least a computing device selects a prescriptive element as a function of minimizing the loss function. This may be performed utilizing any of the methods as described above in reference to FIGS. 1-9.

With continued reference to FIG. 9, at step 940 at least a computing device transmits the selected prescriptive element to a user client device 116. This may be performed utilizing any of the methods as described above in reference to FIGS. 1-9. In an embodiment, at least a computing device may transmit the plurality of prescriptive elements 136 generated by prescriptive generator module 108. Prescriptive elements transmitted to user client device 116 may include cost calculations for a particular prescriptive element. This may help a user may informed decisions and to evaluate thoroughness and treatment selection that a medical professional treating a user may provide. This may also help create transparency with costs a user may receive from an insurance company regarding prescriptive elements. Ultimately this may help increase transparency in the health care system and protect against unnecessary treatments.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
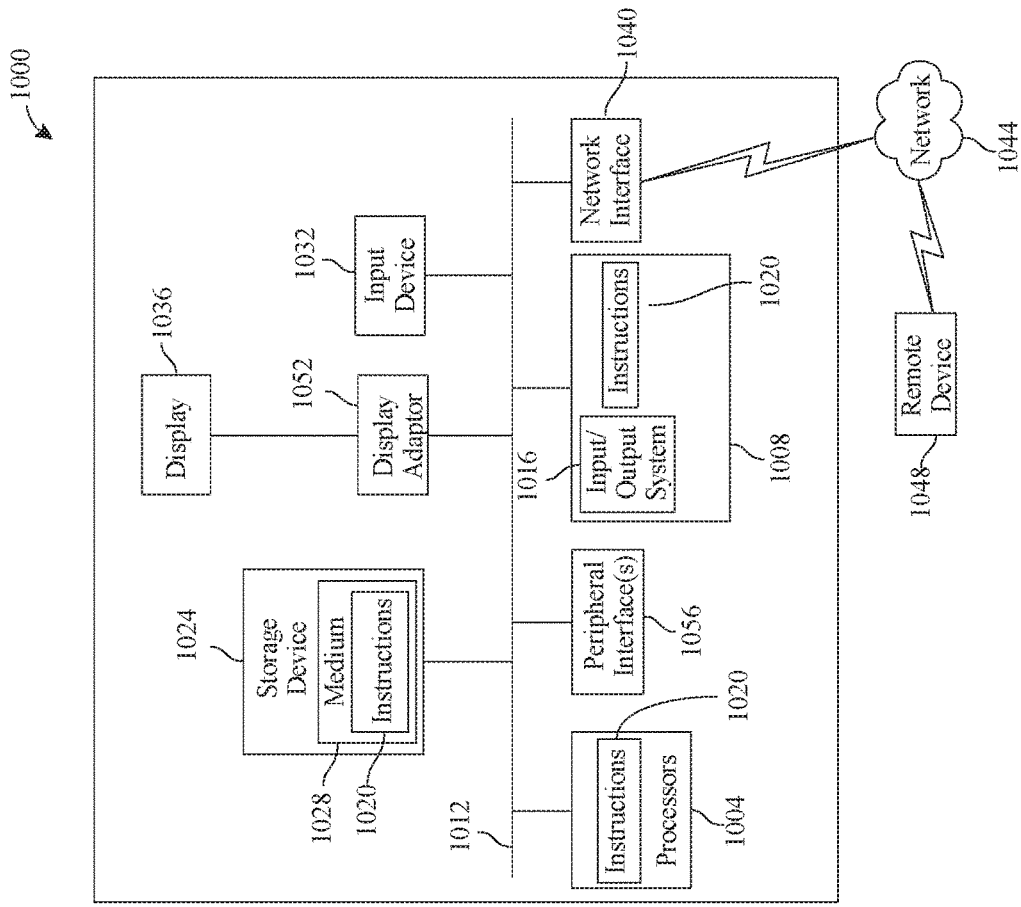
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for selecting a prescriptive element based on user implementation inputs including a computing device wherein the computing device further comprises one or more network interfaces and one or more processors, the system comprising:
    a prescriptive generator module operating on the at least a computing device, the prescriptive generator module designed and configured to:
        receive, from a user client device associated with a user, a diagnosis descriptor wherein the diagnosis descriptor contains a probable medical condition of the user, wherein the probable medical condition of the user comprises a current and a future probable medical condition;
        receive, from a machine-learning database, a diagnosis descriptor training set, wherein the diagnosis descriptor training set comprises a disease classifier training set;
        retrieve at least a prescriptive training datum as a function of the disease classifier training set, wherein at least a portion of the at least a prescriptive training datum correlates the probable medical condition of the user to at least one prescriptive element; and
        generate a prescriptive model using a supervised machine-learning process, wherein the supervised machine-learning process is configured to receive the diagnosis descriptor as an input and output a plurality of prescriptive elements; and
    a loss function module operating on the at least a computing device, the loss function module designed and configured to:
        receive, from the user client device associated with the user, a user implementation response, wherein the user implementation response comprises a prescriptive element indicator comprising data describing a user willingness related to a parameter of a prescriptive element;
        receive, from the prescriptive generator module, the diagnosis descriptor and the plurality of prescriptive elements;
        generate a loss function as a function of the user implementation response and the plurality of prescriptive elements;
        generate at least a classification label as a function of the user implementation response;
        generate a user implementation score as a function of the user implementation response, wherein the user implementation score comprises a user willingness score related to a parameter of a prescriptive element and the plurality of prescriptive elements;
        generate at least a user implementation neutralizer as a function of the at least a classification label and the user implementation score;
        minimize the loss function as a function of the at least a user implementation neutralizer;
        select a prescriptive element from the plurality of prescriptive elements by performing a machine-learning algorithm using a loss function analysis as a function of minimizing the loss function, wherein the selected prescriptive element comprises a price to be paid by a patient associated with the selected prescriptive element; and
        transmit the selected prescriptive element to the user client device associated with the user, wherein the price to be paid by a patient associated with the selected prescriptive element is configured to be displayed on a user device.

2. The system of claim 1, wherein the diagnostic descriptor further comprises a disease classifier, said disease classifier including a disease stage descriptor; and wherein the prescriptive training data is received from a machine-learning database as a function of the disease stage descriptor.

3. The system of claim 1, wherein the prescriptive generator module is further configured to select a second prescriptive model from a machine-learning database as a function of the diagnostic descriptor.

4. The system of claim 1, wherein the prescriptive generator module is further configured to transmit the plurality of prescriptive elements to a user client device.

5. The system of claim 1, wherein the user implementation response further comprises a numerical response reflecting a user willingness score and wherein the loss function module is further configured to generate the loss function further as a function of the user willingness score.

6. The system of claim 1, wherein minimizing the loss function further comprises:
    evaluating the user implementation response to obtain a user implementation factor;
    assigning a weighted variable to the user implementation response as a function of the user implementation factor; and
    minimizing the loss function as a function of the weighted variable.

7. The system of claim 1, wherein minimizing the loss function further comprises:
    generating a plurality of user implementation neutralizers;
    transmitting the plurality of user implementation neutralizers to a user client device;
    receiving a user implementation neutralizer response from the user client device;
    selecting a user implementation neutralizer as a function of the user implementation neutralizer response;

evaluating the implementation response to obtain a user implementation factor comprising a numerical scored response; and minimizing the loss function utilizing the selected user implementation neutralizer.

8. The system of claim 1, wherein the loss function module is further configured to:

receive, from the user client device associated with the user, a user implementation response, wherein the user implementation response comprises a prescriptive allocation standard response, the prescriptive allocation standard response further comprising at least a description of an amount of resources the user intends to devote to a prescriptive element; and generate the loss function as a function of the prescriptive allocation standard response.

9. A method of selecting a prescriptive element based on user implementation inputs the method comprising:

receiving, by a computing device from a user client device, a diagnosis descriptor wherein the diagnosis descriptor contains a probable medical condition of the user, wherein the probable medical condition of the user comprises a current and a future probable medical condition;

receiving, by the at least a computing device from a machine-learning database, a diagnosis descriptor training set, wherein the diagnosis descriptor training set comprises a disease classifier training set;

retrieving, by the at least a computing device from the disease classifier training set, at least a prescriptive training datum, wherein at least a portion of the at least a prescriptive training datum correlates the probable medical condition to at least one prescriptive element;

generating, by the at least a computing device, a prescriptive model using a supervised machine-learning process, wherein the supervised machine-learning process is configured to receive the diagnosis descriptor as an input and output a plurality of prescriptive elements;

receiving, by the at least a computing device from the user client device, a user implementation response, wherein the user implementation response comprises a prescriptive element indicator comprising data describing a user willingness related to a parameter of a prescriptive element;

receiving, by the at least a computing device, the diagnosis descriptor and the plurality of prescriptive elements;

generating, by the at least a computing device, a loss function as a function of the user implementation response and the plurality of prescriptive elements;

generating, by the at least a computing device, at least a classification label as a function of the user implementation response;

generating, by the at least a computing device, a user implementation score as a function of the user implementation response, the user implementation score comprising a user willingness related to a parameter of a prescriptive element and the plurality of prescriptive elements;

generating, by the at least a computing device, at least a user implementation neutralizer as a function of the at least a classification label and the user implementation score;

minimizing, by the at least a computing device, the loss function as a function of the at least a user implementation neutralizer;

selecting, by the at least a computing device, a prescriptive element from the plurality of prescriptive elements by performing a machine-learning algorithm using a loss function analysis as a function of minimizing the loss function, wherein the selected prescriptive element comprises a price to be paid by a patient associated with the selected prescriptive element; and transmitting by the at least a computing device the selected prescriptive element to the user client device, wherein the price to be paid by a patient associated with the selected prescriptive element is configured to be displayed on a user device.

10. The method of claim 9, wherein the diagnostic descriptor further comprises a disease classifier, said disease classifier including a disease stage descriptor; and wherein the prescriptive training data is received from a machine-learning database as a function of the disease stage descriptor.

11. The method of claim 9, wherein receiving prescriptive training data further comprises selecting a second prescriptive model from a machine-learning database as a function of the diagnostic descriptor.

12. The method of claim 9, wherein generating a plurality of prescriptive elements further comprises transmitting the plurality of prescriptive elements to a user client device.

13. The method of claim 9, wherein receiving the user implementation response further comprises receiving a numerical response reflecting a user willingness score and wherein the loss function module is further configured to generate the loss function further as a function of the user willingness score.

14. The method of claim 9, wherein minimizing the loss function further comprises:

evaluating the user implementation response to obtain a user implementation factor;

assigning a weighted variable to the user implementation response as a function of the user implementation factor; and minimizing the loss function as a function of the weighted variable.

15. The method of claim 9, wherein minimizing the loss function further comprises:

generating a plurality of user implementation neutralizers;

transmitting the plurality of user implementation neutralizers to a user client device;

receiving a user implementation neutralizer response from the user client device;

selecting a user implementation neutralizer as a function of the user implementation neutralizer response; and minimizing the loss function utilizing the selected user implementation neutralizer.

16. The method of claim 9, the method further comprising:

receiving, by the at least a computing device from the user client device, a user implementation response, wherein the user implementation response comprises a prescriptive allocation standard response, the prescriptive allocation standard response further comprising at least a description of an amount of resources the user intends to devote to a prescriptive element; and generating, by the at least a computing device, the loss function as a function of the prescriptive allocation standard response.

* * * * *